US010683291B2

(12) United States Patent
Mohan et al.

(10) Patent No.: US 10,683,291 B2
(45) Date of Patent: Jun. 16, 2020

(54) HETEROCYCLIC COMPOUNDS FOR THE TREATMENT OF DISEASE

(71) Applicant: OPPILAN PHARMA LTD., Cambridge (GB)

(72) Inventors: Raju Mohan, Encinitas, CA (US); John Nuss, San Diego, CA (US); Jason Harris, Carlsbad, CA (US)

(73) Assignee: OPPILAN PHARMA LTD., Cambridge (GB)

( * ) Notice: Subject to any disclaimer, the term of this patent is extended or adjusted under 35 U.S.C. 154(b) by 0 days.

(21) Appl. No.: 15/775,723

(22) PCT Filed: Nov. 11, 2016

(86) PCT No.: PCT/US2016/061676
§ 371 (c)(1),
(2) Date: May 11, 2018

(87) PCT Pub. No.: WO2017/083756
PCT Pub. Date: May 18, 2017

(65) Prior Publication Data
US 2019/0241556 A1    Aug. 8, 2019

Related U.S. Application Data

(60) Provisional application No. 62/255,041, filed on Nov. 13, 2015.

(51) Int. Cl.
| | | |
|---|---|---|
| *C07D 471/04* | (2006.01) | |
| *A61P 1/00* | (2006.01) | |
| *A61K 31/41* | (2006.01) | |
| *A61K 31/4245* | (2006.01) | |
| *A61K 31/433* | (2006.01) | |
| *A61P 25/00* | (2006.01) | |

(52) U.S. Cl.
CPC ............ *C07D 471/04* (2013.01); *A61K 31/41* (2013.01); *A61K 31/4245* (2013.01); *A61K 31/433* (2013.01); *A61P 1/00* (2018.01); *A61P 25/00* (2018.01)

(58) Field of Classification Search
CPC .................................................. C07D 471/04
See application file for complete search history.

(56) References Cited

U.S. PATENT DOCUMENTS

| 7,834,039 B2 | 11/2010 | Hobson et al. |
| 2007/0043014 A1 | 2/2007 | Doherty et al. |
| 2010/0160369 A1 | 6/2010 | Canne et al. |
| 2011/0071570 A1 | 3/2011 | Trieu |
| 2011/0207704 A1 | 8/2011 | Cusack et al. |
| 2013/0158001 A1 | 6/2013 | Das et al. |
| 2013/0196966 A1 | 8/2013 | Martinborough et al. |

FOREIGN PATENT DOCUMENTS

| WO | WO-2006131336 A1 | 12/2006 |
| WO | WO-2008076356 A1 | 6/2008 |
| WO | WO-2010065760 A1 | 6/2010 |
| WO | WO-2010117662 A1 | 10/2010 |
| WO | WO-2013059594 A1 | 4/2013 |
| WO | WO-2017083756 A1 | 5/2017 |

OTHER PUBLICATIONS

Silverman, R.B. The Organic Chemistry of Drug Design and Drug Action 1992, Academic: New York, p. 19.*
Rosen "Sphingosine 1-Phosphate Receptor Signaling" Annu. Rev. Biochem. 2009.78:743-768.*
Cruz-Correa "Targeting S1P Receptors, A New Mechanism of Action for Inflammatory Bowel Disease Therapy" Gastroenterology 2016;151:1025-1032.*
Bundgaard. Design and Application of Prodrugs. Textbook of Drug Design and Development. Krosgaard-Larsen and Bundgaard. Chapter 5. pp. 113-191 (1991).
Bundgaard. Means to Enhance Penetration: Prodrugs as a Means to Improve the Delivery of Peptide Drugs. Advanced Drug Delivery Review 8:1-38 (1992).
PCT/US2016/061676 International Preliminary Report on Patentability dated May 24, 2018.
PCT/US2016/061676 International Search Report and Written Opinion dated Jan. 5, 2017.
Science IP Report (4 pgs.) (2016).
Science IP Report (63 pgs.) (2016).
Tully et al. 2-(oxadiazolyl)- and 2-(thiazolyl)imidazo[1,2-a]pyrimidines as agonists and inverse agonists at benzodiazepine receptors. J Med Chem 34:2060-2067 (1991).
Widder et al. Section III: Prodrugs Kinetics. Method in Enzymology. 112:309-396 (1985).

* cited by examiner

*Primary Examiner* — David K O'Dell
(74) *Attorney, Agent, or Firm* — Wilson Sonsini Goodrich & Rosati

(57) ABSTRACT

Described herein are heterocyclic compounds, compositions, and methods for their use for the treatment of disease.

14 Claims, 2 Drawing Sheets

HETEROCYCLIC COMPOUNDS FOR THE TREATMENT OF DISEASE

CROSS-REFERENCE

The present application is a U.S. National Stage entry of PCT application PCT/US2016/061676, filed Nov. 11, 2016, which claims benefit of U.S. Provisional Application No. 62/255,041, filed on Nov. 13, 2015, which are herein incorporated by reference in their entirety.

BACKGROUND OF THE INVENTION

The sphingosine-1-phosphate (S1P) receptors are a class of G protein-coupled receptors that are targets of the lipid signaling molecule sphingosine-1-phosphate. Sphingosine-1-phosphate (S1P) is a bioactive sphingolipid that has been demonstrated to induce many cellular processes, including those that result in platelet aggregation, cell proliferation, cell morphology, tumor-cell invasion, endothelial cell chemotaxis and angiogenesis, cytoskeletal re-arrangements in many cell types to regulate immune cell trafficking, vascular homeostasis and cell communication in the central nervous system (CNS) and in peripheral organ systems. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and SIPS (EDG-8). S1P receptor modulators are compounds which signal as agonists or antagonists at one or more S1P receptors. Since S1P mediates a wide variety of cellular responses, S1P receptor modulators are promising targets for a variety of therapeutic indications.

SUMMARY OF THE INVENTION

Described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for modulating the S1P receptor. In one aspect is the administration of a therapeutically effective amount of at least one S1P receptor modulator described herein to a mammal in the treatment of diseases, disorders or conditions that would benefit from S1P receptor modulation.

In one aspect, provided herein is a compound of Formula (I), or a pharmaceutically acceptable salt or solvate thereof:

Formula (I)

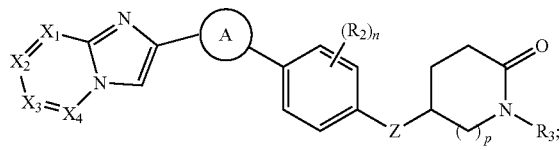

wherein:

$X_1$, $X_2$, $X_3$, and $X_4$ are each $CR_1$; or
$X_1$ is N; $X_2$, $X_3$, and $X_4$ are each $CR_1$; or
$X_2$ is N; $X_1$, $X_3$, and $X_4$ are each $CR_1$; or
$X_3$ is N; $X_1$, $X_2$, and $X_4$ are each $CR_1$; or
$X_4$ is N; $X_1$, $X_2$, and $X_3$ are each $CR_1$;

is selected from

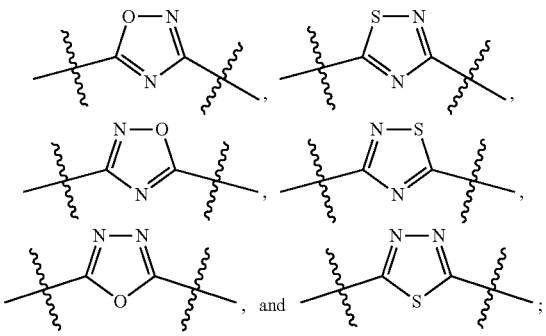

Z is —O—, —S—, —N($R_4$)—, —$CH_2$—, —$OCH_2$—, or —$CH_2O$—;

each $R_1$ is independently selected from the group consisting of hydrogen, halogen, optionally substituted $C_1$-$C_6$alkyl, optionally substituted $C_2$-$C_6$alkenyl, optionally substituted $C_2$-$C_6$alkynyl, optionally substituted aryl, optionally substituted heteroaryl, optionally substituted $C_3$-$C_8$cycloalkyl, optionally substituted —($C_1$-$C_2$alkylene)-($C_3$-$C_8$cycloalkyl), optionally substituted $C_2$-$C_9$heterocycloalkyl, optionally substituted —($C_1$-$C_2$alkylene)-($C_2$-$C_9$heterocycloalkyl), optionally substituted —($C_1$-$C_2$alkylene)-(aryl), optionally substituted —($C_1$-$C_2$alkylene)-(heteroaryl), —$CF_3$, —$OR_{10}$, —N($R_{11}$)$R_{12}$, —N($R_{11}$)S(O)$_2R_{15}$; —N($R_{13}$)N($R_{11}$)$R_{12}$, —N($R_{13}$)N($R_{11}$)S(O)$_2R_{15}$, —C(O)$R_{14}$, —C(O)O$R_{10}$, —C(S)O$R_{10}$, —C(O)S$R_{10}$, —C(O)N($R_{11}$)$R_{12}$, —C(S)N($R_{11}$)$R_{12}$, —C(O)N($R_{11}$)S(O)$_2R_{15}$, —C(S)N($R_{11}$)S(O)$_2R_{15}$, —C(O)N($R_{13}$)N($R_{11}$)$R_{12}$, —C(S)N($R_{13}$)N($R_{11}$)$R_{12}$, and —C(O)N($R_{13}$)N($R_{11}$)S(O)$_2R_{15}$;

each $R_2$ is independently selected from the group consisting of halogen, optionally substituted $C_1$-$C_6$alkyl, —$OR_{20}$, —$SR_{20}$, —N($R_{21}$)$R_{22}$, —C(O)$R_{20}$, —C(O)N($R_{21}$)$R_{22}$, and —N($R_{23}$)C(O)$R_{20}$;

$R_3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted heteroaryl, and optionally substituted —($C_1$-$C_2$alkylene)-(heteroaryl);

$R_4$ is hydrogen or optionally substituted $C_1$-$C_6$alkyl, $R_{10}$, $R_{13}$ and $R_{14}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{11}$ and $R_{12}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{11}$ and $R_{12}$ together with the nitrogen atom to which they are attached, form an optionally substituted $C_2$-$C_9$heterocycloalkyl ring;

$R_{15}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{20}$ and $R_{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{21}$ and $R_{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{21}$ and $R_{22}$ together with the nitrogen atom to which they are attached, form an optionally substituted $C_2$-$C_9$heterocycloalkyl ring;

n is 0-4; and p is 0 or 1.

In one embodiment is a compound of Formula (I), or a pharmaceutically acceptable salt or solvate thereof, wherein $X_1$, $X_2$, $X_3$, and $X_4$ are each $CR_1$. In another embodiment is a compound of Formula (I), or a pharmaceutically acceptable salt or solvate thereof, wherein $X_1$ is N; $X_2$, $X_3$, and $X_4$ are each $CR_1$. In another embodiment is a compound of Formula (I), or a pharmaceutically acceptable salt or solvate thereof, wherein $X_2$ is N; and $X_1$, $X_3$, and $X_4$ are each $CR_1$. In another embodiment is a compound of Formula (I), or a pharmaceutically acceptable salt or solvate thereof, wherein $X_3$ is N; and $X_1$, $X_2$, and $X_4$ are each $CR_1$. In another embodiment is a compound of Formula (I), or a pharmaceutically acceptable salt or solvate thereof, wherein $X_4$ is N; and $X_1$, $X_2$, and $X_3$ are each $CR_1$. In another embodiment is a compound of Formula (I), or a pharmaceutically acceptable salt or solvate thereof, wherein each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (I), or a pharmaceutically acceptable salt or solvate thereof, wherein each $R_1$ is independently selected from the group consisting of hydrogen, halogen, and —$CF_3$. In another embodiment is a compound of Formula (I), or a pharmaceutically acceptable salt or solvate thereof, wherein each $R_2$ is independently selected from the group consisting of halogen, optionally substituted $C_1$-$C_6$alkyl, —$OR_{20}$, and —$N(R_{21})R_{22}$. In another embodiment is a compound of Formula (I), or a pharmaceutically acceptable salt or solvate thereof, wherein each $R_2$ is independently selected from the group consisting of halogen and optionally substituted $C_1$-$C_6$alkyl. In another embodiment is a compound of Formula (I), or a pharmaceutically acceptable salt or solvate thereof, wherein $R_3$ is selected from the group consisting of hydrogen and optionally substituted $C_1$-$C_6$alkyl. In another embodiment is a compound of Formula (I), or a pharmaceutically acceptable salt or solvate thereof, wherein

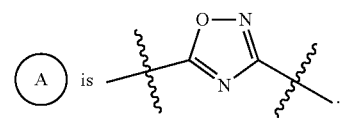

In another embodiment is a compound of Formula (I), or a pharmaceutically acceptable salt or solvate thereof, wherein

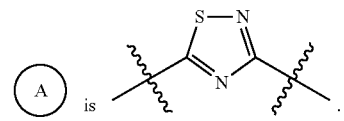

In another embodiment is a compound of Formula (I), or a pharmaceutically acceptable salt or solvate thereof, wherein

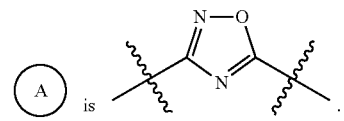

In another embodiment is a compound of Formula (I), or a pharmaceutically acceptable salt or solvate thereof, wherein

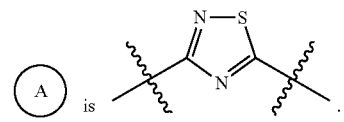

In another embodiment is a compound of Formula (I), or a pharmaceutically acceptable salt or solvate thereof, wherein

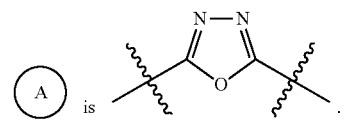

In another embodiment is a compound of Formula (I), or a pharmaceutically acceptable salt or solvate thereof, wherein

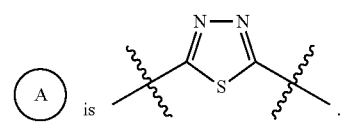

In another embodiment is a compound of Formula (I), or a pharmaceutically acceptable salt or solvate thereof, wherein Z is —O—, —OCH$_2$—, or —CH$_2$O—. In another embodiment is a compound of Formula (I), or a pharmaceutically acceptable salt or solvate thereof, wherein Z is —O—. In another embodiment is a compound of Formula (I), or a pharmaceutically acceptable salt or solvate thereof, wherein Z is —OCH$_2$—. In another embodiment is a compound of Formula (I), or a pharmaceutically acceptable salt or solvate thereof, wherein p is 0. In another embodiment is a compound of Formula (I), or a pharmaceutically acceptable salt or solvate thereof, wherein p is 1. In another embodiment is a compound of Formula (I), or a pharmaceutically acceptable salt or solvate thereof, wherein n is 0. In another embodiment is a compound of Formula (I), or a pharmaceutically acceptable salt or solvate thereof, wherein n is 1. In another embodiment is a compound of Formula (I), or a pharmaceutically acceptable salt or solvate thereof, wherein n is 2.

Any combination of the groups described above or below for the various variables is contemplated herein. Throughout the specification, groups and substituents thereof are chosen by one skilled in the field to provide stable moieties and compounds.

In another aspect, provided herein is a pharmaceutical composition comprising a compound of Formula (I), or a pharmaceutically acceptable salt or solvate thereof, and a pharmaceutically acceptable diluent, excipient or binder. In one embodiment, the pharmaceutical composition comprising the compound of Formula (I), or a pharmaceutically acceptable salt or solvate thereof, is formulated for a route of administration selected from oral administration, parenteral administration, buccal administration, nasal administration, topical administration, or rectal administration.

In another aspect is a method of treating a disease, disorder or condition in a mammal that would benefit from S1P receptor modulation comprising administering to the mammal a therapeutically effective amount of a compound of Formula (I), or a pharmaceutically acceptable salt or solvate thereof.

In another embodiment is a method of treating a disease, disorder or condition in a mammal that would benefit from S1P receptor modulation comprising administering to the mammal a therapeutically effective amount of a compound of Formula (I), or a pharmaceutically acceptable salt or solvate thereof; wherein the disease, disorder or condition in a mammal is selected from multiple sclerosis, ulcerative colitis, and Crohn's disease. In another embodiment is a method of treating a disease, disorder or condition in a mammal that would benefit from S1P receptor modulation comprising administering to the mammal a therapeutically effective amount of a compound of Formula (I), or a pharmaceutically acceptable salt or solvate thereof; wherein the disease, disorder or condition in a mammal is multiple sclerosis. In another embodiment is a method of treating a disease, disorder or condition in a mammal that would benefit from S1P receptor modulation comprising administering to the mammal a therapeutically effective amount of a compound of Formula (I), or a pharmaceutically acceptable salt or solvate thereof; wherein the disease, disorder or condition in a mammal is ulcerative colitis. In another embodiment is a method of treating a disease, disorder or condition in a mammal that would benefit from S1P receptor modulation comprising administering to the mammal a therapeutically effective amount of a compound of Formula (I), or a pharmaceutically acceptable salt or solvate thereof; wherein the disease, disorder or condition in a mammal is Crohn's disease.

In a further embodiment is a method of treating a disease, disorder or condition in a mammal that would benefit from S1P receptor modulation comprising administering to the mammal a therapeutically effective amount of a compound of Formula (I), or a pharmaceutically acceptable salt or solvate thereof; wherein the disease, disorder or condition in a mammal is rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

In another embodiment is the use of a compound of Formula (I), (Ia), (Ib), (Ic), (Id), (Ie), (II), (IIa), (IIb), (IIc), (IId), or (IIe) in the manufacture of a medicament for the treatment of a disease, disorder, or condition that would benefit from S1P receptor modulation. In another embodiment is the use of a S1P receptor modulator in the manufacture of a medicament for use in the treatment of a disease, disorder or condition in a mammal, wherein the disease, disorder or condition in a mammal is rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

In another aspect is a method of modulating S1P receptor activity comprising contacting the S1P receptor, or portion thereof, with a compound of Formula (I), or a pharmaceutically acceptable salt or solvate thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
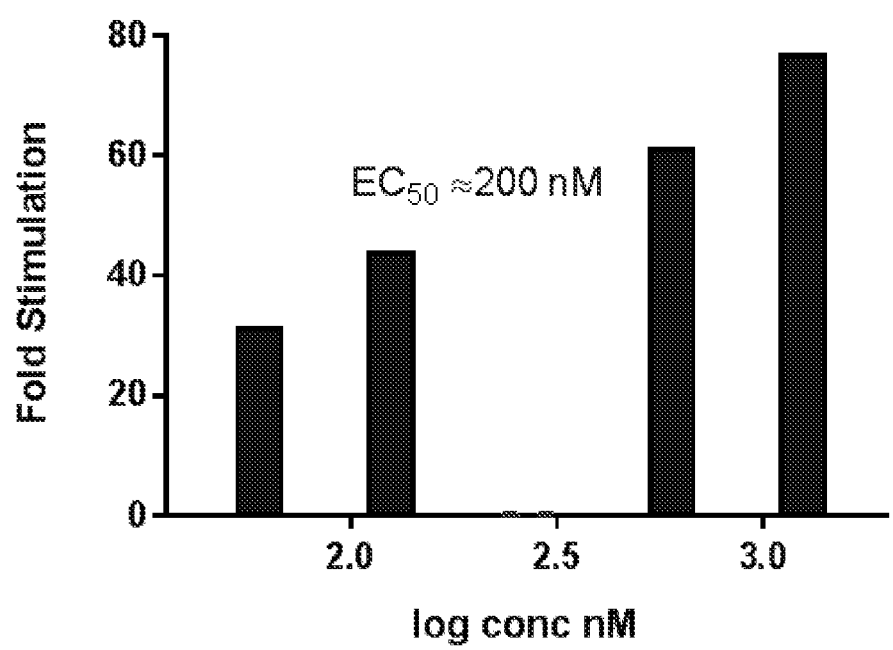
FIG. 1 shows the cellular potency for a compound of Formula (I) described herein in the Ca$^{2+}$ flux assay.

The sphingosine-1-phosphate receptors regulate fundamental biological processes such as cell proliferation, angiogenesis, migration, cytoskeleton organization, endothelial cell chemotaxis, immune cell trafficking and mitogenesis. Sphingosine-1-phosphate receptors are also involved in immune-modulation and directly involved in suppression of innate immune responses from T cells. Sphingosine-1-phosphate (S1P) receptors are divided into five subtypes: S1PR1, S1PR2, S1PR3, S1PR4 and S1PR5. They are expressed in a wide variety of tissues, with each subtype exhibiting different cell specificity, although they are found at their highest density on leukocytes.

Described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for modulating the S1P receptor. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating S1P receptor subtypes. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating two S1P receptor subtypes. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating a single S1P receptor subtype. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating S1P receptor subtype 1. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating S1P receptor subtype 2. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating S1P receptor subtype 3. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating S1P receptor subtype 4. In some embodiments described herein are compounds of Formula (I), (Ia), (Ib), (Ic), (Id), (Ie), (II), (IIa), (IIb), (IIc), (IId), or (IIe), pharmaceutical compositions that include such compounds, and methods of use thereof, for selectively modulating S1P receptor subtype 5.

In another aspect is the administration of at least one S1P receptor modulator described herein to a mammal in the treatment of diseases, disorders or conditions that would benefit from S1P receptor modulation. In some embodiments is the administration of at least one S1P receptor modulator described herein to a mammal in the treatment of diseases, disorders or conditions that would benefit from the selective modulation of S1P receptor subtypes. In some embodiments is the administration of at least one S1P receptor modulator described herein to a mammal in the treatment of diseases, disorders or conditions that would benefit from the selective modulation of two S1P receptor subtypes. In some embodiments is the administration of at least one S1P receptor modulator described herein to a mammal in the treatment of diseases, disorders or conditions that would benefit from the selective modulation of one S1P receptor subtype. In some embodiments is the administration of at least one S1P receptor modulator described herein to a mammal in the treatment of diseases, disorders or conditions that would benefit from the selective modulation of S1P receptor subtype 1. In some embodiments is the administration of at least one S1P receptor modulator described herein to a mammal in the treatment of diseases, disorders or conditions that would benefit from the selective modulation of S1P receptor subtype 2. In some embodiments is the administration of at least one S1P receptor modulator described herein to a mammal in the treatment of diseases, disorders or conditions that would benefit from the selective modulation of S1P receptor subtype 3. In some embodiments is the administration of at least one S1P receptor modulator described herein to a mammal in the treatment of diseases, disorders or conditions that would benefit from the selective modulation of S1P receptor subtype 4. In some embodiments is the administration of at least one S1P receptor modulator described herein to a mammal in the treatment of diseases, disorders or conditions that would benefit from the selective modulation of S1P receptor subtype 5.

In some embodiments, is a method of modulating S1P receptor activity comprising contacting S1P receptor, or portion thereof, with a compound of Formula (I), (Ia), (Ib), (Ic), (Id), (Ie), (II), (IIa), (IIb), (IIc), (IId), or (IIe), or a pharmaceutically acceptable salt or solvate thereof. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 1 agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 2 agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 3 agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 4 agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 5 agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor partial agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 1 partial agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 2 partial agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 3 partial agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 4 partial agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 5 partial agonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor antagonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 1 antagonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 2 antagonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 3 antagonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 4 antagonist. In some embodiments, the compound of Formula (I), (Ia), (Ib), (Ic), (Id), (Ie), (II), (IIa), (IIb), (IIc), (IId), or (IIe), or a pharmaceutically acceptable salt or solvate thereof, is an S1P receptor subtype 5 antagonist.

Compounds

In one aspect, provided herein is a compound of Formula (I), or a pharmaceutically acceptable salt or solvate thereof:

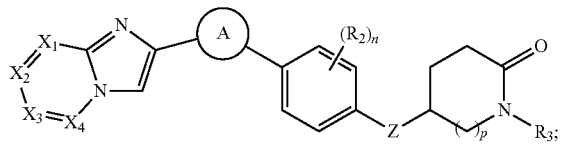

Formula (I)

wherein:
$X_1$, $X_2$, $X_3$, and $X_4$ are each $CR_1$; or
$X_1$ is N; $X_2$, $X_3$, and $X_4$ are each $CR_1$; or
$X_2$ is N; $X_1$, $X_3$, and $X_4$ are each $CR_1$; or
$X_3$ is N; $X_1$, $X_2$, and $X_4$ are each $CR_1$; or
$X_4$ is N; $X_1$, $X_2$, and $X_3$ are each $CR_1$;

is selected from

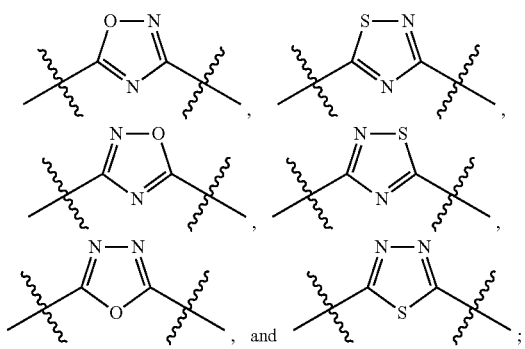

Z is —O—, —S—, —N($R_4$)—, —CH$_2$—, —OCH$_2$—, or —CH$_2$O—;

each $R_1$ is independently selected from the group consisting of hydrogen, halogen, optionally substituted $C_1$-$C_6$alkyl, optionally substituted $C_2$-$C_6$alkenyl, optionally substituted $C_2$-$C_6$alkynyl, optionally substituted aryl, optionally substituted heteroaryl, optionally substituted $C_3$-$C_8$cycloalkyl, optionally substituted —($C_1$-$C_2$alkylene)-($C_3$-$C_8$cycloalkyl), optionally substituted $C_2$-$C_9$heterocycloalkyl, optionally substituted —($C_1$-$C_2$alkylene)-($C_2$-$C_9$heterocycloalkyl), optionally substituted —($C_1$-$C_2$alkylene)-(aryl), optionally substituted —($C_1$-$C_2$alkylene)-(heteroaryl), —CF$_3$, —OR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted $C_1$-$C_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted heteroaryl, and optionally substituted —($C_1$-$C_2$alkylene)-(heteroaryl);

R$_4$ is hydrogen or optionally substituted $C_1$-$C_6$alkyl,

R$_{10}$, R$_{13}$ and R$_{14}$ are each independently selected from the group consisting of hydrogen, optionally substituted $C_1$-$C_6$alkyl, optionally substituted $C_2$-$C_6$alkenyl, optionally substituted $C_2$-$C_6$ alkynyl, optionally substituted $C_3$-$C_8$ cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R$_{11}$ and R$_{12}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally R$_{11}$ and R$_{12}$ together with the nitrogen atom to which they are attached, form an optionally substituted $C_2$-$C_9$heterocycloalkyl ring;

R$_{15}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$ alkylene)-(aryl), optionally substituted $C_2$-$C_9$heterocycloalkyl, optionally substituted heteroaryl, and optionally substituted —($C_1$-$C_2$ alkylene)-(heteroaryl);

R$_{20}$ and R$_{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{21}$ and $R_{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{21}$ and $R_{22}$ together with the nitrogen atom to which they are attached, form an optionally substituted $C_2$-$C_9$heterocycloalkyl ring;

n is 0-4; and p is 0 or 1.

In one embodiment is a compound of Formula (I) wherein $X_1$, $X_2$, $X_3$, and $X_4$ are each $CR_1$. In another embodiment is a compound of Formula (I) wherein $X_1$, $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (I) wherein $X_1$, $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (I) wherein $X_1$, $X_2$, $X_3$, and $X_4$ are each $CR_1$; and each $R_1$ is independently selected from the group consisting of hydrogen, halogen, and —$CF_3$.

In another embodiment is a compound of Formula (I) wherein $X_1$ is N; and $X_2$, $X_3$, and $X_4$ are each $CR_1$. In another embodiment is a compound of Formula (I) wherein $X_1$ is N; and $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (I) wherein $X_1$ is N; and $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (I) wherein $X_1$ is N; and $X_2$, $X_3$, and $X_4$ are each $CR_1$; and each $R_1$ is independently selected from the group consisting of hydrogen, halogen, and —$CF_3$.

In another embodiment is a compound of Formula (I) wherein $X_2$ is N; and $X_1$, $X_3$, and $X_4$ are each $CR_1$. In another embodiment is a compound of Formula (I) wherein $X_2$ is N; and $X_1$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (I) wherein $X_2$ is N; and $X_1$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (I) wherein $X_2$ is N; and $X_1$, $X_3$, and $X_4$ are each $CR_1$; and each $R_1$ is independently selected from the group consisting of hydrogen, halogen, and —$CF_3$.

In another embodiment is a compound of Formula (I) wherein $X_3$ is N; and $X_1$, $X_2$, and $X_4$ are each $CR_1$. In another embodiment is a compound of Formula (I) wherein $X_3$ is N; and $X_1$, $X_2$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (I) wherein $X_3$ is N; and $X_1$, $X_2$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (I) wherein $X_3$ is N; and $X_1$, $X_2$, and $X_4$ are each $CR_1$; and each $R_1$ is independently selected from the group consisting of hydrogen, halogen, and —$CF_3$.

In another embodiment is a compound of Formula (I) wherein $X_4$ is N; and $X_1$, $X_2$, and $X_3$ are each $CR_1$. In another embodiment is a compound of Formula (I) wherein $X_4$ is N; and $X_1$, $X_2$, and $X_3$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (I) wherein $X_4$ is N; and $X_1$, $X_2$, and $X_3$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (I) wherein $X_4$ is N; and $X_1$, $X_2$, and $X_3$ are each $CR_1$; and each $R_1$ is independently selected from the group consisting of hydrogen, halogen, and —$CF_3$.

In another embodiment is a compound of Formula (I) wherein n is 3 and each $R_2$ is independently selected from the group consisting of halogen, optionally substituted $C_1$-$C_6$alkyl, —$OR_{20}$, and —$N(R_{21})R_{22}$. In another embodiment is a compound of Formula (I) wherein n is 3 and each $R_2$ is independently selected from the group consisting of halogen and optionally substituted $C_1$-$C_6$alkyl. In another embodiment is a compound of Formula (I) wherein n is 2 and each $R_2$ is independently selected from the group consisting of halogen, optionally substituted $C_1$-$C_6$alkyl, —$OR_{20}$, and —$N(R_{21})R_{22}$. In another embodiment is a compound of Formula (I) wherein n is 2 and each $R_2$ is independently selected from the group consisting of halogen and optionally substituted $C_1$-$C_6$alkyl. In another embodiment is a compound of Formula (I) wherein n is 1 and $R_2$ is selected from the group consisting of halogen, optionally substituted $C_1$-$C_6$alkyl, —$OR_{20}$, and —$N(R_{21})R_{22}$. In another embodiment is a compound of Formula (I) wherein n is 1 and $R_2$ is selected from the group consisting of halogen and optionally substituted $C_1$-$C_6$alkyl. In another embodiment is a compound of Formula (I) wherein n is 0.

In another embodiment is a compound of Formula (I) wherein $R_3$ is selected from the group consisting of hydrogen and optionally substituted $C_1$-$C_6$alkyl. In another embodiment is a compound of Formula (I) wherein $R_3$ is hydrogen. In another embodiment is a compound of Formula (I) wherein $R_3$ is optionally substituted $C_1$-$C_6$alkyl. In another embodiment is a compound of Formula (I) wherein $R_3$ is methyl.

In another embodiment is a compound of Formula (I) wherein

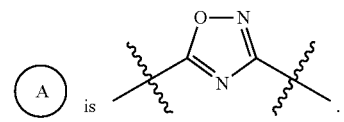

In another embodiment is a compound of Formula (I) wherein

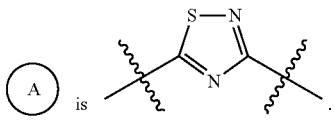

In another embodiment is a compound of Formula (I) wherein

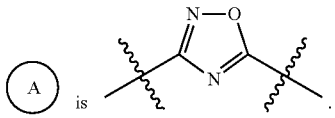

In another embodiment is a compound of Formula (I) wherein

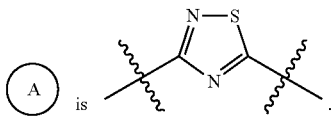

In another embodiment is a compound of Formula (I) wherein

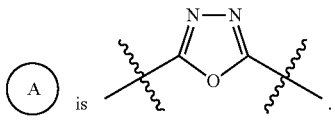

In another embodiment is a compound of Formula (I) wherein

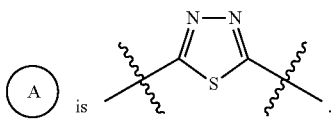

In another embodiment is a compound of Formula (I) wherein Z is —O—, —OCH$_2$—, or —CH$_2$O—. In another embodiment is a compound of Formula (I) wherein Z is —O—. In another embodiment is a compound of Formula (I) wherein Z is —OCH$_2$—. In another embodiment is a compound of Formula (I) wherein Z is —CH$_2$O—. In another embodiment is a compound of Formula (I) wherein Z is —S—. In another embodiment is a compound of Formula (I) wherein Z is —CH$_2$—. In another embodiment is a compound of Formula (I) wherein Z is —N(R$_4$)—. In another embodiment is a compound of Formula (I) wherein Z is —N(H)—. In another embodiment is a compound of Formula (I) wherein Z is —N(CH$_3$)—.

In another embodiment is a compound of Formula (I) wherein p is 0. In another embodiment is a compound of Formula (I) wherein p is 1.

In some embodiments provided herein, the compound of Formula (I) has the structure of Formula (Ia), or a pharmaceutically acceptable salt or solvate thereof:

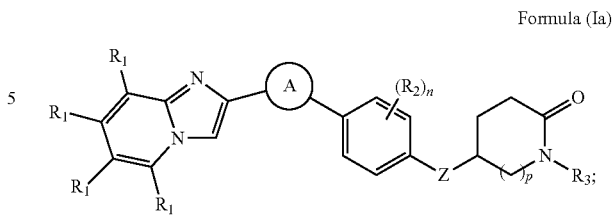

Formula (Ia)

wherein:

is selected from

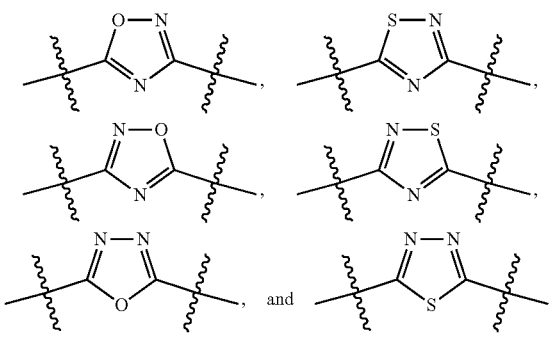

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —N(R$_{11}$)R$_{12}$, —N(R$_{11}$)S(O)$_2$R$_{15}$, —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R₁₀, R₁₃ and R₁₄ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R₁₁ and R₁₂ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally R₁₁ and R₁₂ together with the nitrogen atom to which they are attached, form an optionally substituted $C_2$-$C_9$heterocycloalkyl ring;

R₁₅ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R₂₀ and R₂₃ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

R₂₁ and R₂₂ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally R₂₁ and R₂₂ together with the nitrogen atom to which they are attached, form an optionally substituted $C_2$-$C_9$heterocycloalkyl ring;

n is 0-4; and p is 0 or 1.

In one embodiment is a compound of Formula (Ia) wherein each R₁ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (Ia) wherein each R₁ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (Ia) wherein each R₁ is independently selected from the group consisting of hydrogen, halogen, and —$CF_3$.

In another embodiment is a compound of Formula (Ia) wherein n is 3 and each R₂ is independently selected from the group consisting of halogen, optionally substituted $C_1$-$C_6$alkyl, —$OR_{20}$, and —$N(R_{21})R_{22}$. In another embodiment is a compound of Formula (Ia) wherein n is 3 and each R₂ is independently selected from the group consisting of halogen and optionally substituted $C_1$-$C_6$alkyl. In another embodiment is a compound of Formula (Ia) wherein n is 2 and each R₂ is independently selected from the group consisting of halogen, optionally substituted $C_1$-$C_6$alkyl, —$OR_{20}$, and —$N(R_{21})R_{22}$. In another embodiment is a compound of Formula (Ia) wherein n is 2 and each R₂ is independently selected from the group consisting of halogen and optionally substituted $C_1$-$C_6$alkyl. In another embodiment is a compound of Formula (Ia) wherein n is 1 and R₂ is selected from the group consisting of halogen, optionally substituted $C_1$-$C_6$alkyl, —$OR_{20}$, and —$N(R_{21})R_{22}$. In another embodiment is a compound of Formula (Ia) wherein n is 1 and R₂ is selected from the group consisting of halogen and optionally substituted $C_1$-$C_6$alkyl. In another embodiment is a compound of Formula (Ia) wherein n is 0.

In another embodiment is a compound of Formula (Ia) wherein R₃ is selected from the group consisting of hydrogen and optionally substituted $C_1$-$C_6$alkyl. In another embodiment is a compound of Formula (Ia) wherein R₃ is hydrogen. In another embodiment is a compound of Formula (Ia) wherein R₃ is optionally substituted $C_1$-$C_6$alkyl. In another embodiment is a compound of Formula (Ia) wherein R₃ is methyl.

In another embodiment is a compound of Formula (Ia) wherein

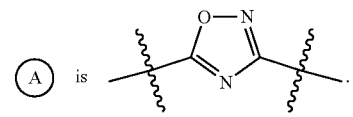

In another embodiment is a compound of Formula (Ia) wherein

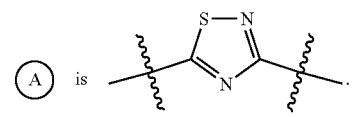

In another embodiment is a compound of Formula (Ia) wherein

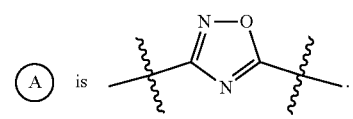

In another embodiment is a compound of Formula (Ia) wherein

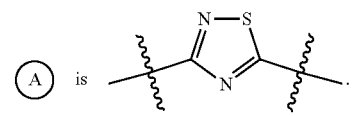

In another embodiment is a compound of Formula (Ia) wherein

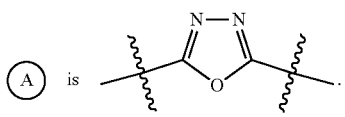

In another embodiment is a compound of Formula (Ia) wherein

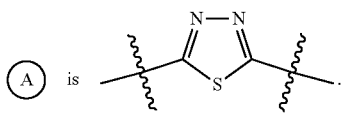

In another embodiment is a compound of Formula (Ia) wherein Z is —O—, —OCH$_2$—, or —CH$_2$O—. In another embodiment is a compound of Formula (Ia) wherein Z is —O—. In another embodiment is a compound of Formula (Ia) wherein Z is —OCH$_2$—. In another embodiment is a compound of Formula (Ia) wherein Z is —CH$_2$O—. In another embodiment is a compound of Formula (Ia) wherein Z is —S—. In another embodiment is a compound of Formula (Ia) wherein Z is —CH$_2$—. In another embodiment is a compound of Formula (Ia) wherein Z is —N(R$_4$)—. In another embodiment is a compound of Formula (Ia) wherein Z is —N(H)—. In another embodiment is a compound of Formula (Ia) wherein Z is —N(CH$_3$)—.

In another embodiment is a compound of Formula (Ia) wherein p is 0. In another embodiment is a compound of Formula (Ia) wherein p is 1.

In some embodiments provided herein, the compound of Formula (I) has the structure of Formula (Ib), or a pharmaceutically acceptable salt or solvate thereof:

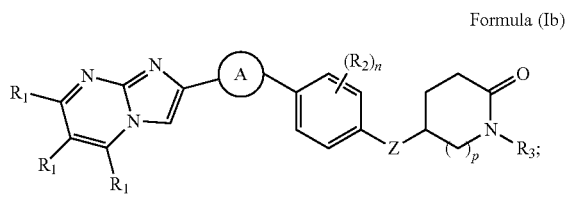

Formula (Ib)

wherein:

is selected from

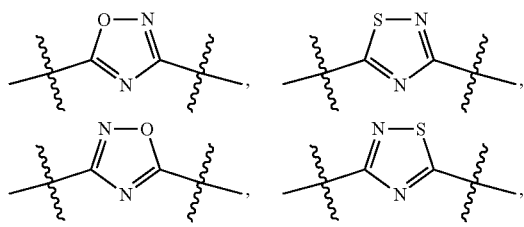

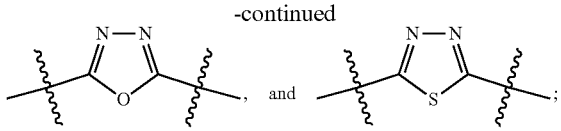

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{11}$ and R$_{12}$ together with the nitrogen atom to which they are attached, form an optionally substituted C$_2$-C$_9$heterocycloalkyl ring;

R$_{15}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_8$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{20}$ and R$_{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{21}$ and R$_{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{21}$ and R$_{22}$ together with the nitrogen atom to which they are attached, form an optionally substituted C$_2$-C$_9$heterocycloalkyl ring;

n is 0-4; and p is 0 or 1.

In one embodiment is a compound of Formula (Ib) wherein each R$_1$ is independently selected from the group consisting of hydrogen, halogen, optionally substituted C$_1$-C$_6$alkyl, —CF$_3$, —OR$_{10}$, —N(R$_{11}$)R$_{12}$, —C(O)R$_{14}$, —C(O)OR$_{10}$, and —C(O)N(R$_{11}$)R$_{12}$. In another embodiment is a compound of Formula (Ib) wherein each R$_1$ is independently selected from the group consisting of hydrogen, halogen, optionally substituted C$_1$-C$_6$alkyl, —CF$_3$, —OR$_{10}$, and —N(R$_{11}$)R$_{12}$. In another embodiment is a compound of Formula (Ib) wherein each R$_1$ is independently selected from the group consisting of hydrogen, halogen, and —CF$_3$.

In another embodiment is a compound of Formula (Ib) wherein n is 3 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Ib) wherein n is 3 and each R$_2$ is independently selected from the group consisting of halogen and optionally substituted C$_1$-C$_6$alkyl. In another embodiment is a compound of Formula (Ib) wherein n is 2 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Ib) wherein n is 2 and each R$_2$ is independently selected from the group consisting of halogen and optionally substituted C$_1$-C$_6$alkyl. In another embodiment is a compound of Formula (Ib) wherein n is 1 and R$_2$ is selected from the group consisting of halogen, optionally substituted C$_1$-C$_6$alkyl, —OR$_{20}$, and —N(R$_{21}$)R$_{22}$. In another embodiment is a compound of Formula (Ib) wherein n is 1 and R$_2$ is selected from the group consisting of halogen and optionally substituted C$_1$-C$_6$alkyl. In another embodiment is a compound of Formula (Ib) wherein n is 0.

In another embodiment is a compound of Formula (Ib) wherein R$_3$ is selected from the group consisting of hydrogen and optionally substituted C$_1$-C$_6$alkyl. In another embodiment is a compound of Formula (Ib) wherein R$_3$ is hydrogen. In another embodiment is a compound of Formula (Ib) wherein R$_3$ is optionally substituted C$_1$-C$_6$alkyl. In another embodiment is a compound of Formula (Ib) wherein R$_3$ is methyl.

In another embodiment is a compound of Formula (Ib) wherein

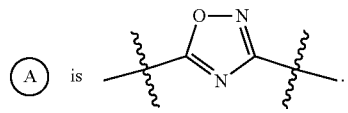

In another embodiment is a compound of Formula (Ib) wherein

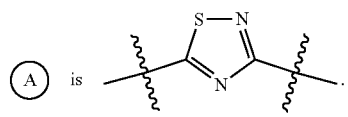

In another embodiment is a compound of Formula (Ib) wherein

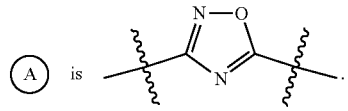

In another embodiment is a compound of Formula (Ib) wherein

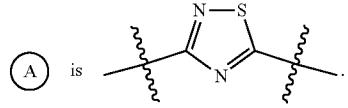

In another embodiment is a compound of Formula (Ib) wherein

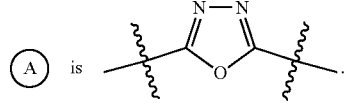

In another embodiment is a compound of Formula (Ib) wherein

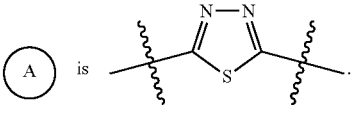

In another embodiment is a compound of Formula (Ib) wherein Z is —O—, —OCH$_2$—, or —CH$_2$O—. In another embodiment is a compound of Formula (Ib) wherein Z is —O—. In another embodiment is a compound of Formula (Ib) wherein Z is —OCH$_2$—. In another embodiment is a compound of Formula (Ib) wherein Z is —CH$_2$O—. In another embodiment is a compound of Formula (Ib) wherein Z is —S—. In another embodiment is a compound of Formula (Ib) wherein Z is —CH$_2$—. In another embodiment is a compound of Formula (Ib) wherein Z is —N(R$_4$)—. In another embodiment is a compound of Formula (Ib) wherein Z is —N(H)—. In another embodiment is a compound of Formula (Ib) wherein Z is —N(CH$_3$)—.

In another embodiment is a compound of Formula (Ib) wherein p is 0. In another embodiment is a compound of Formula (Ib) wherein p is 1.

In some embodiments provided herein, the compound of Formula (I) has the structure of Formula (Ic), or a pharmaceutically acceptable salt or solvate thereof:

Formula (Ic)

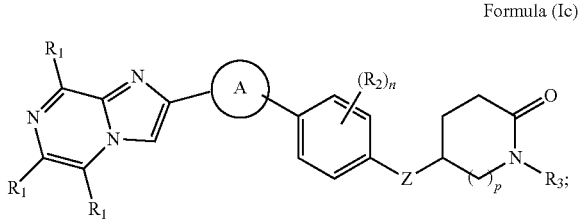

wherein:

is selected from

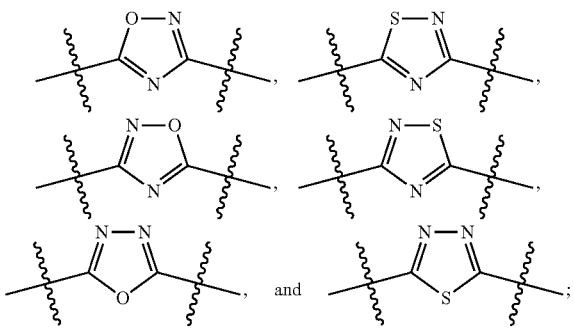

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{11}$ and R$_{12}$ together with the nitrogen atom to which they are attached, form an optionally substituted C$_2$-C$_9$heterocycloalkyl ring;

R$_{15}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_8$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{20}$ and R$_{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{21}$ and R$_{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{21}$ and R$_{22}$ together with the nitrogen atom to which they are attached, form an optionally substituted C$_2$-C$_9$heterocycloalkyl ring;

n is 0-4; and p is 0 or 1.

In one embodiment is a compound of Formula (Ic) wherein each R$_1$ is independently selected from the group consisting of hydrogen, halogen, optionally substituted C$_1$-C$_6$alkyl, —CF$_3$, —OR$_{10}$, —N(R$_{11}$)R$_{12}$, —C(O)R$_{14}$, —C(O)OR$_{10}$, and —C(O)N(R$_{11}$)R$_{12}$. In another embodiment is a compound of Formula (Ic) wherein each R$_1$ is independently selected from the group consisting of hydrogen, halogen, optionally substituted C$_1$-C$_6$alkyl, —CF$_3$, —OR$_{10}$, and —N(R$_{11}$)R$_{12}$. In another embodiment is a compound of Formula (Ic) wherein each R$_1$ is independently selected from the group consisting of hydrogen, halogen, and —CF$_3$.

In another embodiment is a compound of Formula (Ic) wherein n is 3 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Ic) wherein n is 3 and each R$_2$ is independently selected from the group consisting of halogen and optionally substituted C$_1$-C$_6$alkyl. In another embodiment is a compound of Formula (Ic) wherein n is 2 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Ic) wherein n is 2 and each R$_2$ is independently selected from the group consisting of halogen and optionally substituted C$_1$-C$_6$alkyl. In another embodiment is a compound of Formula (Ic) wherein n is 1 and R$_2$ is selected from the group consisting of halogen, optionally substituted C$_1$-C$_6$alkyl, —OR$_{20}$, and —N(R$_{21}$)R$_{22}$. In another embodiment is a compound of Formula (Ic) wherein n is 1 and R$_2$ is selected from the group consisting of halogen and optionally substituted C$_1$-C$_6$alkyl. In another embodiment is a compound of Formula (Ic) wherein n is 0.

In another embodiment is a compound of Formula (Ic) wherein R$_3$ is selected from the group consisting of hydrogen and optionally substituted C$_1$-C$_6$alkyl. In another embodiment is a compound of Formula (Ic) wherein R$_3$ is hydrogen. In another embodiment is a compound of Formula (Ic) wherein R$_3$ is optionally substituted C$_1$-C$_6$alkyl. In another embodiment is a compound of Formula (Ic) wherein R$_3$ is methyl.

In another embodiment is a compound of Formula (Ic) wherein

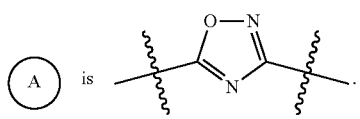

In another embodiment is a compound of Formula (Ic) wherein

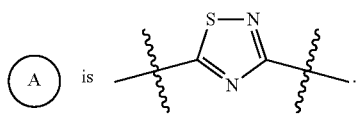

In another embodiment is a compound of Formula (Ic) wherein

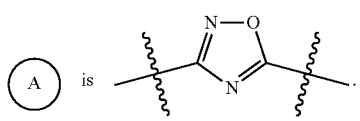

In another embodiment is a compound of Formula (Ic) wherein

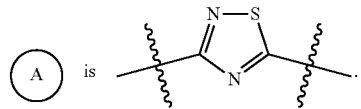

In another embodiment is a compound of Formula (Ic) wherein

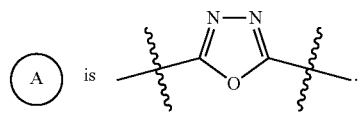

In another embodiment is a compound of Formula (Ic) wherein

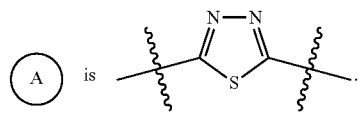

In another embodiment is a compound of Formula (Ic) wherein Z is —O—, —OCH$_2$—, or —CH$_2$O—. In another embodiment is a compound of Formula (Ic) wherein Z is —O—. In another embodiment is a compound of Formula (Ic) wherein Z is —OCH$_2$—. In another embodiment is a compound of Formula (Ic) wherein Z is —CH$_2$O—. In another embodiment is a compound of Formula (Ic) wherein Z is —S—. In another embodiment is a compound of Formula (Ic) wherein Z is —CH$_2$—. In another embodiment is a compound of Formula (Ic) wherein Z is —N(R$_4$)—. In another embodiment is a compound of Formula (Ic) wherein Z is —N(H)—. In another embodiment is a compound of Formula (Ic) wherein Z is —N(CH$_3$)—.

In another embodiment is a compound of Formula (Ic) wherein p is 0. In another embodiment is a compound of Formula (Ic) wherein p is 1.

In some embodiments provided herein, the compound of Formula (I) has the structure of Formula (Id), or a pharmaceutically acceptable salt or solvate thereof:

Formula (Id)

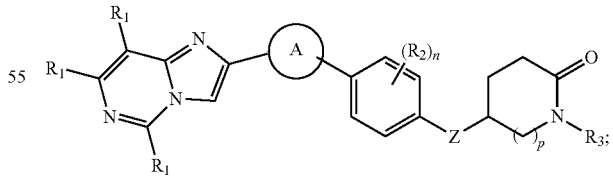

wherein:

is selected from

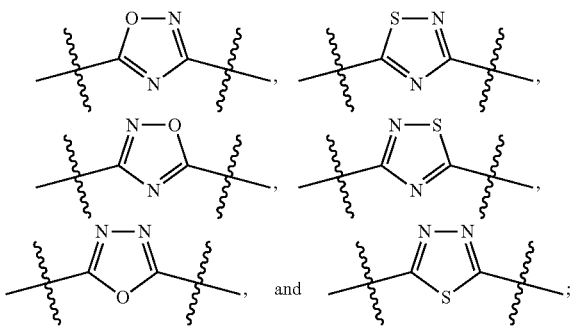

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{10}$, —SR$_{10}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$ alkynyl, optionally substituted C$_3$-C$_8$ cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{11}$ and R$_{12}$ together with the nitrogen atom to which they are attached, form an optionally substituted C$_2$-C$_9$heterocycloalkyl ring;

R$_{15}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_8$ cycloalkyl, optionally substituted aryl optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$ alkylene)-(heteroaryl);

R$_{20}$ and R$_{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{21}$ and R$_{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{21}$ and R$_{22}$ together with the nitrogen atom to which they are attached, form an optionally substituted C$_2$-C$_9$heterocycloalkyl ring;

n is 0-4; and p is 0 or 1.

In one embodiment is a compound of Formula (Id) wherein each R$_1$ is independently selected from the group consisting of hydrogen, halogen, optionally substituted C$_1$-C$_6$alkyl, —CF$_3$, —OR$_{10}$, —N(R$_{11}$)R$_{12}$, —C(O)R$_{14}$, —C(O)OR$_{10}$, and —C(O)N(R$_{11}$)R$_{12}$. In another embodiment is a compound of Formula (Id) wherein each R$_1$ is independently selected from the group consisting of hydrogen, halogen, optionally substituted C$_1$-C$_6$alkyl, —CF$_3$, —OR$_{10}$, and —N(R$_{11}$)R$_{12}$. In another embodiment is a compound of Formula (Id) wherein each R$_1$ is independently selected from the group consisting of hydrogen, halogen, and —CF$_3$.

In another embodiment is a compound of Formula (Id) wherein n is 3 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Id) wherein n is 3 and each R$_2$ is independently selected from the group consisting of halogen and optionally substituted C$_1$-C$_6$alkyl. In another embodiment is a compound of Formula (Id) wherein n is 2 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Id) wherein n is 2 and each R$_2$ is independently selected from the group consisting of halogen and optionally substituted C$_1$-C$_6$alkyl. In another embodiment is a compound of Formula (Id) wherein n is 1 and R$_2$ is selected from the group consisting of halogen, optionally substituted C$_1$-C$_6$alkyl, —OR$_{20}$, and —N(R$_{21}$)R$_{22}$. In another embodiment is a compound of Formula (Id) wherein n is 1 and R$_2$ is selected from the group consisting of halogen and optionally substituted C$_1$-C$_6$alkyl. In another embodiment is a compound of Formula (Id) wherein n is 0.

In another embodiment is a compound of Formula (Id) wherein R₃ is selected from the group consisting of hydrogen and optionally substituted C₁-C₆alkyl. In another embodiment is a compound of Formula (Id) wherein R₃ is hydrogen. In another embodiment is a compound of Formula (Id) wherein R₃ is optionally substituted C₁-C₆alkyl. In another embodiment is a compound of Formula (Id) wherein R₃ is methyl.

In another embodiment is a compound of Formula (Id) wherein

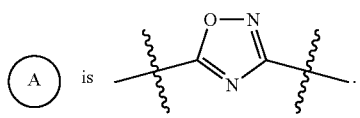

In another embodiment is a compound of Formula (Id) wherein

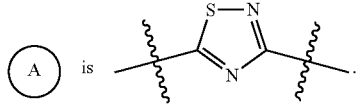

In another embodiment is a compound of Formula (Id) wherein

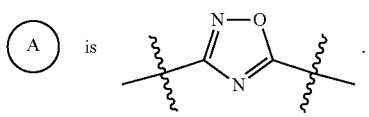

In another embodiment is a compound of Formula (Id) wherein

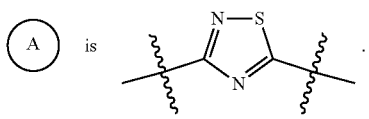

In another embodiment is a compound of Formula (Id) wherein

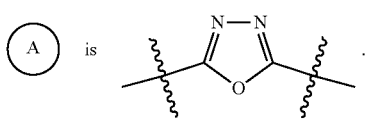

In another embodiment is a compound of Formula (Id) wherein

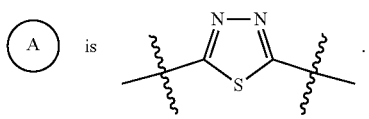

In another embodiment is a compound of Formula (Id) wherein Z is —O—, —OCH₂—, or —CH₂O—. In another embodiment is a compound of Formula (Id) wherein Z is —O—. In another embodiment is a compound of Formula (Id) wherein Z is —OCH₂—. In another embodiment is a compound of Formula (Id) wherein Z is —CH₂O—. In another embodiment is a compound of Formula (Id) wherein Z is —S—. In another embodiment is a compound of Formula (Id) wherein Z is —CH₂—. In another embodiment is a compound of Formula (Id) wherein Z is —N(R₄)—. In another embodiment is a compound of Formula (Id) wherein Z is —N(H)—. In another embodiment is a compound of Formula (Id) wherein Z is —N(CH₃)—.

In another embodiment is a compound of Formula (Id) wherein p is 0. In another embodiment is a compound of Formula (Id) wherein p is 1.

In some embodiments provided herein, the compound of Formula (I) has the structure of Formula (Ie), or a pharmaceutically acceptable salt or solvate thereof:

Formula (Ie)

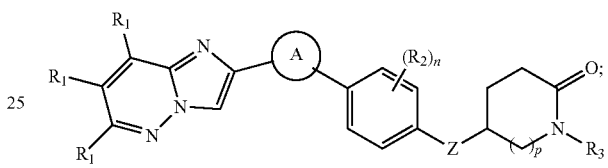

wherein:

is selected from

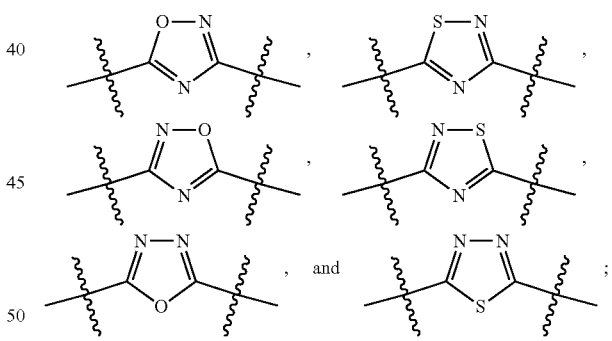

Z is —O—, —S—, —N(R₄)—, —CH₂—, —OCH₂—, or —CH₂O—;

each R₁ is independently selected from the group consisting of hydrogen, halogen, optionally substituted C₁-C₆alkyl, optionally substituted C₂-C₆alkenyl, optionally substituted C₂-C₆alkynyl, optionally substituted aryl, optionally substituted heteroaryl, optionally substituted C₃-C₈cycloalkyl, optionally substituted —(C₁-C₂alkylene)-(C₃-C₈cycloalkyl), optionally substituted C₂-C₉heterocycloalkyl, optionally substituted —(C₁-C₂alkylene)-(C₂-C₉heterocycloalkyl), optionally substituted —(C₁-C₂alkylene)-(aryl), optionally substituted —(C₁-C₂alkylene)-(heteroaryl), —CF₃, —OR₁₀, —SR₁₀, —N(R₁₁)R₁₂, —N(R₁₁)S(O)₂R₁₅; —N(R₁₃)N(R₁₁)R₁₂, —N(R₁₃)N(R₁₁)S(O)₂R₁₅, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{11}$ and R$_{12}$ together with the nitrogen atom to which they are attached, form an optionally substituted C$_2$-C$_9$heterocycloalkyl ring;

R$_{15}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_8$ cycloalkyl, optionally substituted aryl optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$ alkylene)-(heteroaryl);

R$_{20}$ and R$_{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$ alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{21}$ and R$_{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$ alkylene)-(heteroaryl); or optionally R$_{21}$ and R$_{22}$ together with the nitrogen atom to which they are attached, form an optionally substituted C$_2$-C$_9$heterocycloalkyl ring;

n is 0-4; and p is 0 or 1.

In one embodiment is a compound of Formula (Ie) wherein each R$_1$ is independently selected from the group consisting of hydrogen, halogen, optionally substituted C$_1$-C$_6$alkyl, —CF$_3$, —OR$_{10}$, —N(R$_{11}$)R$_{12}$, —C(O)R$_{14}$, —C(O)OR$_{10}$, and —C(O)N(R$_{11}$)R$_{12}$. In another embodiment is a compound of Formula (Ie) wherein each R$_1$ is independently selected from the group consisting of hydrogen, halogen, optionally substituted C$_1$-C$_6$alkyl, —CF$_3$, —OR$_{10}$, and —N(R$_{11}$)R$_u$. In another embodiment is a compound of Formula (Ie) wherein each R$_1$ is independently selected from the group consisting of hydrogen, halogen, and —CF$_3$.

In another embodiment is a compound of Formula (Ie) wherein n is 3 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Ie) wherein n is 3 and each R$_2$ is independently selected from the group consisting of halogen and optionally substituted C$_1$-C$_6$alkyl. In another embodiment is a compound of Formula (Ie) wherein n is 2 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (Ie) wherein n is 2 and each R$_2$ is independently selected from the group consisting of halogen and optionally substituted C$_1$-C$_6$alkyl. In another embodiment is a compound of Formula (Ie) wherein n is 1 and R$_2$ is selected from the group consisting of halogen, optionally substituted C$_1$-C$_6$alkyl, —OR$_{20}$, and —N(R$_{21}$)R$_{22}$. In another embodiment is a compound of Formula (Ie) wherein n is 1 and R$_2$ is selected from the group consisting of halogen and optionally substituted C$_1$-C$_6$alkyl. In another embodiment is a compound of Formula (Ie) wherein n is 0.

In another embodiment is a compound of Formula (Ie) wherein R$_3$ is selected from the group consisting of hydrogen and optionally substituted C$_1$-C$_6$alkyl. In another embodiment is a compound of Formula (Ie) wherein R$_3$ is hydrogen. In another embodiment is a compound of Formula (Ie) wherein R$_3$ is optionally substituted C$_1$-C$_6$alkyl. In another embodiment is a compound of Formula (Ie) wherein R$_3$ is methyl.

In another embodiment is a compound of Formula (Ie) wherein

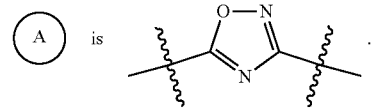

In another embodiment is a compound of Formula (Ie) wherein

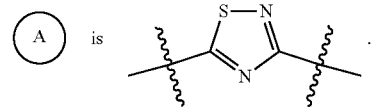

In another embodiment is a compound of Formula (Ie) wherein

A is 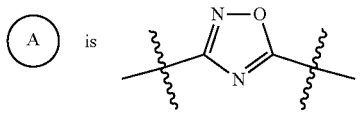.

In another embodiment is a compound of Formula (Ie) wherein

A is 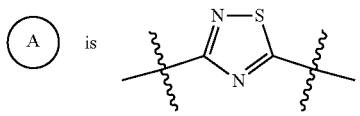.

In another embodiment is a compound of Formula (Ie) wherein

A is 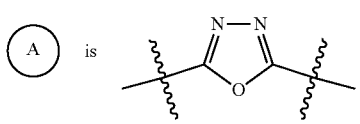.

In another embodiment is a compound of Formula (Ie) wherein

A is 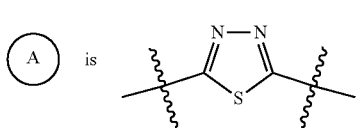.

In another embodiment is a compound of Formula (Ie) wherein Z is —O—, —OCH$_2$—, or —CH$_2$O—. In another embodiment is a compound of Formula (Ie) wherein Z is —O—. In another embodiment is a compound of Formula (Ie) wherein Z is —OCH$_2$—. In another embodiment is a compound of Formula (Ie) wherein Z is —CH$_2$O—. In another embodiment is a compound of Formula (Ie) wherein Z is —S—. In another embodiment is a compound of Formula (Ie) wherein Z is —CH$_2$—. In another embodiment is a compound of Formula (Ie) wherein Z is —N(R$_4$)—. In another embodiment is a compound of Formula (Ie) wherein Z is —N(H)—. In another embodiment is a compound of Formula (Ie) wherein Z is —N(CH$_3$)—.

In another embodiment is a compound of Formula (Ie) wherein p is 0. In another embodiment is a compound of Formula (Ie) wherein p is 1.

In one aspect, provided herein is a compound of Formula (II), or a pharmaceutically acceptable salt or solvate thereof:

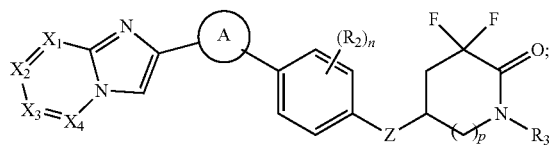

Formula (II)

wherein:
X$_1$, X$_2$, X$_3$, and X$_4$ are each CR$_1$; or
X$_1$ is N; X$_2$, X$_3$, and X$_4$ are each CR$_1$; or
X$_2$ is N; X$_1$, X$_3$, and X$_4$ are each CR$_1$; or
X$_3$ is N; X$_1$, X$_2$, and X$_4$ are each CR$_1$; or
X$_4$ is N; X$_1$, X$_2$, and X$_3$ are each CR$_1$;

 is selected from

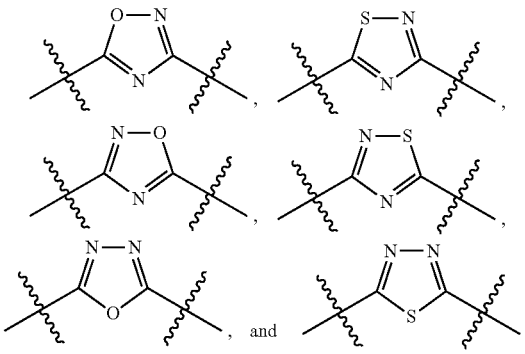

Z is —O—, —S—, —N(R$_4$)—, —CH$_2$—, —OCH$_2$—, or —CH$_2$O—;
each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;
each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;
R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);
R$_4$ is hydrogen or optionally substituted C$_1$-C$_6$alkyl,
R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —($C_1$-$C_2$alkylene)-(heteroaryl);

$R_{11}$ and $R_{12}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{11}$ and $R_{12}$ together with the nitrogen atom to which they are attached, form an optionally substituted $C_2$-$C_9$heterocycloalkyl ring;

$R_{15}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{20}$ and $R_{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{21}$ and $R_{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{21}$ and $R_{22}$ together with the nitrogen atom to which they are attached, form an optionally substituted $C_2$-$C_9$heterocycloalkyl ring;

n is 0-4; and p is 0 or 1.

In one embodiment is a compound of Formula (II) wherein $X_1$, $X_2$, $X_3$, and $X_4$ are each $CR_1$. In another embodiment is a compound of Formula (II) wherein $X_1$, $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (II) wherein $X_1$, $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (II) wherein $X_1$, $X_2$, $X_3$, and $X_4$ are each $CR_1$; and each $R_1$ is independently selected from the group consisting of hydrogen, halogen, and —$CF_3$.

In another embodiment is a compound of Formula (II) wherein $X_1$ is N; and $X_2$, $X_3$, and $X_4$ are each $CR_1$. In another embodiment is a compound of Formula (II) wherein $X_1$ is N; and $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (II) wherein $X_1$ is N; and $X_2$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (II) wherein $X_1$ is N; and $X_2$, $X_3$, and $X_4$ are each $CR_1$; and each $R_1$ is independently selected from the group consisting of hydrogen, halogen, and —$CF_3$.

In another embodiment is a compound of Formula (II) wherein $X_2$ is N; and $X_1$, $X_3$, and $X_4$ are each $CR_1$. In another embodiment is a compound of Formula (II) wherein $X_2$ is N; and $X_1$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (II) wherein $X_2$ is N; and $X_1$, $X_3$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (II) wherein $X_2$ is N; and $X_1$, $X_3$, and $X_4$ are each $CR_1$; and each $R_1$ is independently selected from the group consisting of hydrogen, halogen, and —$CF_3$.

In another embodiment is a compound of Formula (II) wherein $X_3$ is N; and $X_1$, $X_2$, and $X_4$ are each $CR_1$. In another embodiment is a compound of Formula (II) wherein $X_3$ is N; and $X_1$, $X_2$, and $X_4$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (II) wherein $X_3$ is N; and $X_1$, $X_2$, and $X_4$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (II) wherein $X_3$ is N; and $X_1$, $X_2$, and $X_4$ are each $CR_1$; and each $R_1$ is independently selected from the group consisting of hydrogen, halogen, and —$CF_3$.

In another embodiment is a compound of Formula (II) wherein $X_4$ is N; and $X_1$, $X_2$, and $X_3$ are each $CR_1$. In another embodiment is a compound of Formula (II) wherein $X_4$ is N; and $X_1$, $X_2$, and $X_3$ are each $CR_1$; and each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (II) wherein $X_4$ is N; and $X_1$, $X_2$, and $X_3$ are each $CR_1$; and each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (II) wherein $X_4$ is N; and $X_1$, $X_2$, and $X_3$ are each $CR_1$; and each $R_1$ is independently selected from the group consisting of hydrogen, halogen, and —$CF_3$.

In another embodiment is a compound of Formula (II) wherein n is 3 and each $R_2$ is independently selected from the group consisting of halogen, optionally substituted $C_1$-$C_6$alkyl, —$OR_{20}$, and —$N(R_{21})R_{22}$. In another embodiment is a compound of Formula (II) wherein n is 3 and each $R_2$ is independently selected from the group consisting of halogen and optionally substituted $C_1$-$C_6$alkyl. In another embodiment is a compound of Formula (II) wherein n is 2 and each $R_2$ is independently selected from the group consisting of halogen, optionally substituted $C_1$-$C_6$alkyl, —OR₂₀, and —N(R₂₁)R₂₂. In another embodiment is a compound of Formula (II) wherein n is 2 and each R₂ is independently selected from the group consisting of halogen and optionally substituted C₁-C₆alkyl. In another embodiment is a compound of Formula (II) wherein n is 1 and R₂ is selected from the group consisting of halogen, optionally substituted C₁-C₆alkyl, —OR₂₀, and —N(R₂₁)R₂₂. In another embodiment is a compound of Formula (II) wherein n is 1 and R₂ is selected from the group consisting of halogen and optionally substituted C₁-C₆alkyl. In another embodiment is a compound of Formula (II) wherein n is 0.

In another embodiment is a compound of Formula (II) wherein R₃ is selected from the group consisting of hydrogen and optionally substituted C₁-C₆alkyl. In another embodiment is a compound of Formula (II) wherein R₃ is hydrogen. In another embodiment is a compound of Formula (II) wherein R₃ is optionally substituted C₁-C₆alkyl. In another embodiment is a compound of Formula (II) wherein R₃ is methyl.

In another embodiment is a compound of Formula (II) wherein

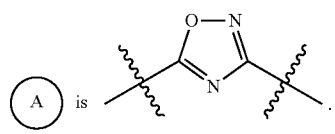

In another embodiment is a compound of Formula (II) wherein

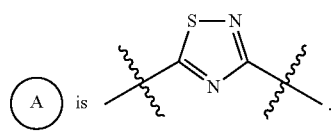

In another embodiment is a compound of Formula (II) wherein

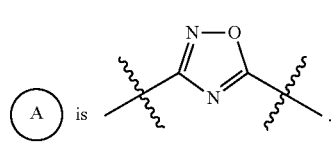

In another embodiment is a compound of Formula (II) wherein

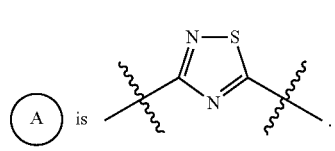

In another embodiment is a compound of Formula (II) wherein

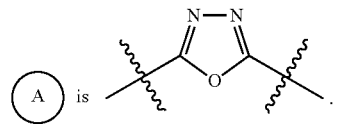

In another embodiment is a compound of Formula (II) wherein

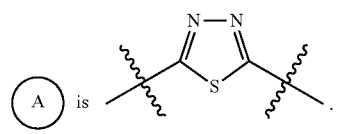

In another embodiment is a compound of Formula (II) wherein Z is —O—, —OCH₂—, or —CH₂O—. In another embodiment is a compound of Formula (II) wherein Z is —O—. In another embodiment is a compound of Formula (II) wherein Z is —OCH₂—. In another embodiment is a compound of Formula (II) wherein Z is —CH₂O—. In another embodiment is a compound of Formula (II) wherein Z is —S—. In another embodiment is a compound of Formula (II) wherein Z is —CH₂—. In another embodiment is a compound of Formula (II) wherein Z is —N(R₄)—. In another embodiment is a compound of Formula (II) wherein Z is —N(H)—. In another embodiment is a compound of Formula (II) wherein Z is —N(CH₃)—.

In another embodiment is a compound of Formula (II) wherein p is 0. In another embodiment is a compound of Formula (II) wherein p is 1.

In some embodiments provided herein, the compound of Formula (II) has the structure of Formula (IIa), or a pharmaceutically acceptable salt or solvate thereof:

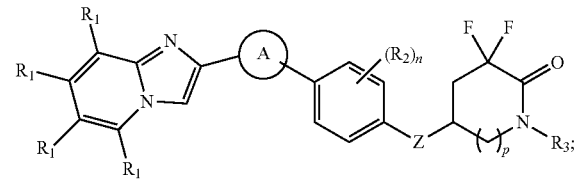

Formula (IIa)

wherein:

is selected from

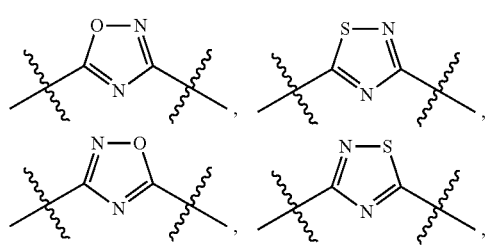

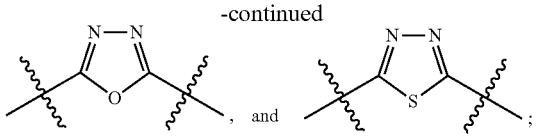
, and

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{11}$ and R$_{12}$ together with the nitrogen atom to which they are attached, form an optionally substituted C$_2$-C$_9$heterocycloalkyl ring;

R$_{15}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_8$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{20}$ and R$_{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{21}$ and R$_{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{21}$ and R$_{22}$ together with the nitrogen atom to which they are attached, form an optionally substituted C$_2$-C$_9$heterocycloalkyl ring;

n is 0-4; and p is 0 or 1.

In one embodiment is a compound of Formula (IIa) wherein each R$_1$ is independently selected from the group consisting of hydrogen, halogen, optionally substituted C$_1$-C$_6$alkyl, —CF$_3$, —OR$_{10}$, —N(R$_{11}$)R$_{12}$, —C(O)R$_{14}$, —C(O)OR$_{10}$, and —C(O)N(R$_{11}$)R$_{12}$. In another embodiment is a compound of Formula (IIa) wherein each R$_1$ is independently selected from the group consisting of hydrogen, halogen, optionally substituted C$_1$-C$_6$alkyl, —CF$_3$, —OR$_{10}$, and —N(R$_{11}$)R$_{12}$. In another embodiment is a compound of Formula (IIa) wherein each R$_1$ is independently selected from the group consisting of hydrogen, halogen, and —CF$_3$.

In another embodiment is a compound of Formula (IIa) wherein n is 3 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (IIa) wherein n is 3 and each R$_2$ is independently selected from the group consisting of halogen and optionally substituted C$_1$-C$_6$alkyl. In another embodiment is a compound of Formula (IIa) wherein n is 2 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (IIa) wherein n is 2 and each R$_2$ is independently selected from the group consisting of halogen and optionally substituted C$_1$-C$_6$alkyl. In another embodiment is a compound of Formula (IIa) wherein n is 1 and R$_2$ is selected from the group consisting of halogen, optionally substituted C$_1$-C$_6$alkyl, —OR$_{20}$, and —N(R$_{21}$)R$_{22}$. In another embodiment is a compound of Formula (IIa) wherein n is 1 and R$_2$ is selected from the group consisting of halogen and optionally substituted C$_1$-C$_6$alkyl. In another embodiment is a compound of Formula (IIa) wherein n is 0.

In another embodiment is a compound of Formula (IIa) wherein R$_3$ is selected from the group consisting of hydrogen and optionally substituted C$_1$-C$_6$alkyl. In another embodiment is a compound of Formula (IIa) wherein R$_3$ is hydrogen. In another embodiment is a compound of Formula (IIa) wherein R$_3$ is optionally substituted C$_1$-C$_6$alkyl. In another embodiment is a compound of Formula (IIa) wherein R$_3$ is methyl.

In another embodiment is a compound of Formula (IIa) wherein

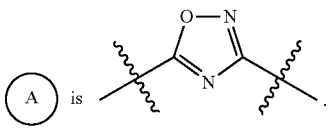

In another embodiment is a compound of Formula (IIa) wherein

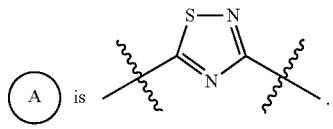

In another embodiment is a compound of Formula (IIa) wherein

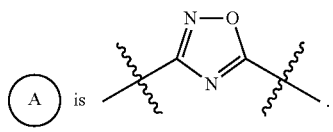

In another embodiment is a compound of Formula (IIa) wherein

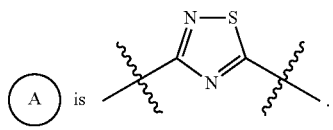

In another embodiment is a compound of Formula (IIa) wherein

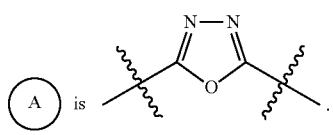

In another embodiment is a compound of Formula (IIa) wherein

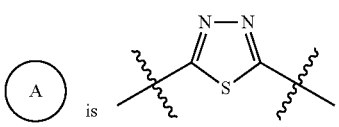

In another embodiment is a compound of Formula (IIa) wherein Z is —O—, —OCH$_2$—, or —CH$_2$O—. In another embodiment is a compound of Formula (IIa) wherein Z is —O—. In another embodiment is a compound of Formula (IIa) wherein Z is —OCH$_2$—. In another embodiment is a compound of Formula (IIa) wherein Z is —CH$_2$O—. In another embodiment is a compound of Formula (IIa) wherein Z is —S—. In another embodiment is a compound of Formula (IIa) wherein Z is —CH$_2$—. In another embodiment is a compound of Formula (IIa) wherein Z is —N(R$_4$)—. In another embodiment is a compound of Formula (IIa) wherein Z is —N(H)—. In another embodiment is a compound of Formula (IIa) wherein Z is —N(CH$_3$)—.

In another embodiment is a compound of Formula (IIa) wherein p is 0. In another embodiment is a compound of Formula (IIa) wherein p is 1.

In some embodiments provided herein, the compound of Formula (II) has the structure of Formula (IIb), or a pharmaceutically acceptable salt or solvate thereof:

Formula (IIb)

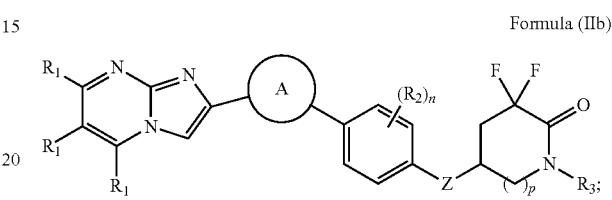

wherein:

is selected from

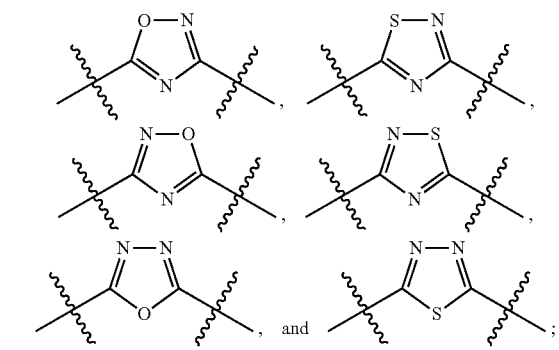

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each $R_2$ is independently selected from the group consisting of halogen, optionally substituted $C_1$-$C_6$alkyl, —$OR_{20}$, —$SR_{20}$, —$N(R_{21})R_{22}$, —$C(O)R_{20}$, —$C(O)N(R_{21})R_{22}$, and —$N(R_{23})C(O)R_{20}$;

$R_3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted heteroaryl, and optionally substituted —($C_1$-$C_2$alkylene)-(heteroaryl);

$R_4$ is hydrogen or optionally substituted $C_1$-$C_6$alkyl, $R_{10}$, $R_{13}$ and $R_{14}$ are each independently selected from the group consisting of hydrogen, optionally substituted $C_1$-$C_6$alkyl, optionally substituted $C_2$-$C_6$alkenyl, optionally substituted $C_2$-$C_6$ alkynyl, optionally substituted $C_3$-$C_8$cycloalkyl, optionally substituted aryl, optionally substituted —($C_1$-$C_2$ alkylene)-(aryl), optionally substituted $C_2$-$C_9$heterocycloalkyl, optionally substituted heteroaryl, and optionally substituted —($C_1$-$C_2$alkylene)-(heteroaryl);

$R_{11}$ and $R_{12}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$ alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{11}$ and $R_{12}$ together with the nitrogen atom to which they are attached, form an optionally substituted $C_2$-$C_9$heterocycloalkyl ring;

$R_{15}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$ alkylene)-(aryl), optionally substituted $C_2$-$C_9$heterocycloalkyl, optionally substituted heteroaryl, and optionally substituted —($C_1$-$C_2$ alkylene)-(heteroaryl);

$R_{20}$ and $R_{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$ alkylene)-(aryl), optionally substituted $C_2$-$C_9$heterocycloalkyl, optionally substituted heteroaryl, and optionally substituted —($C_1$-$C_2$alkylene)-(heteroaryl);

$R_{21}$ and $R_{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$ alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{21}$ and $R_{22}$ together with the nitrogen atom to which they are attached, form an optionally substituted $C_2$-$C_9$heterocycloalkyl ring;

n is 0-4; and p is 0 or 1.

In one embodiment is a compound of Formula (IIb) wherein each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (IIb) wherein each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (IIb) wherein each $R_1$ is independently selected from the group consisting of hydrogen, halogen, and —$CF_3$.

In another embodiment is a compound of Formula (IIb) wherein n is 3 and each $R_2$ is independently selected from the group consisting of halogen, optionally substituted $C_1$-$C_6$alkyl, —$OR_{20}$, and —$N(R_{21})R_{22}$. In another embodiment is a compound of Formula (IIb) wherein n is 3 and each $R_2$ is independently selected from the group consisting of halogen and optionally substituted $C_1$-$C_6$alkyl. In another embodiment is a compound of Formula (IIb) wherein n is 2 and each $R_2$ is independently selected from the group consisting of halogen, optionally substituted $C_1$-$C_6$alkyl, —$OR_{20}$, and —$N(R_{21})R_{22}$. In another embodiment is a compound of Formula (IIb) wherein n is 2 and each $R_2$ is independently selected from the group consisting of halogen and optionally substituted $C_1$-$C_6$alkyl. In another embodiment is a compound of Formula (IIb) wherein n is 1 and $R_2$ is selected from the group consisting of halogen, optionally substituted $C_1$-$C_6$alkyl, —$OR_{20}$, and —$N(R_{21})R_{22}$. In another embodiment is a compound of Formula (IIb) wherein n is 1 and $R_2$ is selected from the group consisting of halogen and optionally substituted $C_1$-$C_6$alkyl. In another embodiment is a compound of Formula (IIb) wherein n is 0.

In another embodiment is a compound of Formula (IIb) wherein $R_3$ is selected from the group consisting of hydrogen and optionally substituted $C_1$-$C_6$alkyl. In another embodiment is a compound of Formula (IIb) wherein $R_3$ is hydrogen. In another embodiment is a compound of Formula (IIb) wherein $R_3$ is optionally substituted $C_1$-$C_6$alkyl. In another embodiment is a compound of Formula (IIb) wherein $R_3$ is methyl.

In another embodiment is a compound of Formula (IIb) wherein

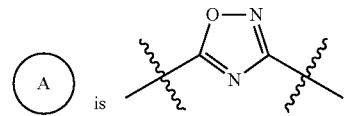

.

In another embodiment is a compound of Formula (IIb) wherein

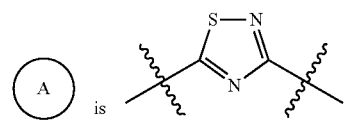

.

In another embodiment is a compound of Formula (IIb) wherein

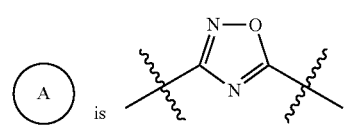

.

In another embodiment is a compound of Formula (IIb) wherein

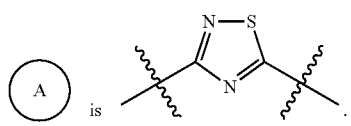

In another embodiment is a compound of Formula (IIb) wherein

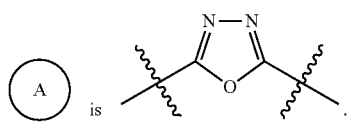

In another embodiment is a compound of Formula (IIb) wherein

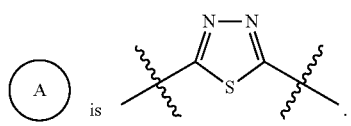

In another embodiment is a compound of Formula (IIb) wherein Z is —O—, —OCH$_2$—, or —CH$_2$O—. In another embodiment is a compound of Formula (IIb) wherein Z is —O—. In another embodiment is a compound of Formula (IIb) wherein Z is —OCH$_2$—. In another embodiment is a compound of Formula (IIb) wherein Z is —CH$_2$O—. In another embodiment is a compound of Formula (IIb) wherein Z is —S—. In another embodiment is a compound of Formula (IIb) wherein Z is —CH$_2$—. In another embodiment is a compound of Formula (IIb) wherein Z is —N(R$_4$)—. In another embodiment is a compound of Formula (IIb) wherein Z is —N(H)—. In another embodiment is a compound of Formula (IIb) wherein Z is —N(CH$_3$)—.

In another embodiment is a compound of Formula (IIb) wherein p is 0. In another embodiment is a compound of Formula (IIb) wherein p is 1.

In some embodiments provided herein, the compound of Formula (II) has the structure of Formula (IIc), or a pharmaceutically acceptable salt or solvate thereof:

Formula (IIc)

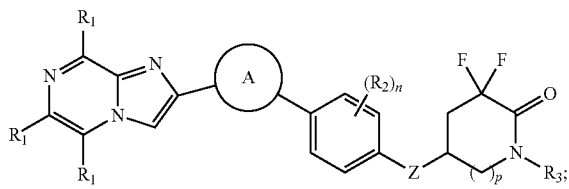

wherein:

is selected from

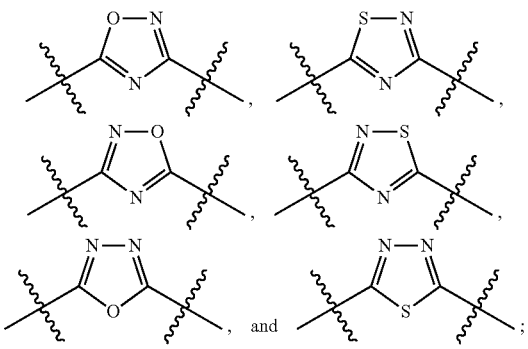

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —($C_1$-$C_2$alkylene)-(heteroaryl); or optionally $R_{11}$ and $R_{12}$ together with the nitrogen atom to which they are attached, form an optionally substituted $C_2$-$C_9$heterocycloalkyl ring;

$R_{15}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{20}$ and $R_{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{21}$ and $R_{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{21}$ and $R_{22}$ together with the nitrogen atom to which they are attached, form an optionally substituted $C_2$-$C_9$heterocycloalkyl ring;

n is 0-4; and p is 0 or 1.

In one embodiment is a compound of Formula (IIc) wherein each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (IIc) wherein each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (IIc) wherein each $R_1$ is independently selected from the group consisting of hydrogen, halogen, and —$CF_3$.

In another embodiment is a compound of Formula (IIc) wherein n is 3 and each $R_2$ is independently selected from the group consisting of halogen, optionally substituted $C_1$-$C_6$alkyl, —$OR_{20}$, and —$N(R_{21})R_{22}$. In another embodiment is a compound of Formula (IIc) wherein n is 3 and each $R_2$ is independently selected from the group consisting of halogen and optionally substituted $C_1$-$C_6$alkyl. In another embodiment is a compound of Formula (IIc) wherein n is 2 and each $R_2$ is independently selected from the group consisting of halogen, optionally substituted $C_1$-$C_6$alkyl, —$OR_{20}$, and —$N(R_{21})R_{22}$. In another embodiment is a compound of Formula (IIc) wherein n is 2 and each $R_2$ is independently selected from the group consisting of halogen and optionally substituted $C_1$-$C_6$alkyl. In another embodiment is a compound of Formula (IIc) wherein n is 1 and $R_2$ is selected from the group consisting of halogen, optionally substituted $C_1$-$C_6$alkyl, —$OR_{20}$, and —$N(R_{21})R_{22}$. In another embodiment is a compound of Formula (IIc) wherein n is 1 and $R_2$ is selected from the group consisting of halogen and optionally substituted $C_1$-$C_6$alkyl. In another embodiment is a compound of Formula (IIc) wherein n is 0.

In another embodiment is a compound of Formula (IIc) wherein $R_3$ is selected from the group consisting of hydrogen and optionally substituted $C_1$-$C_6$alkyl. In another embodiment is a compound of Formula (IIc) wherein $R_3$ is hydrogen. In another embodiment is a compound of Formula (IIc) wherein $R_3$ is optionally substituted $C_1$-$C_6$alkyl. In another embodiment is a compound of Formula (IIc) wherein $R_3$ is methyl.

In another embodiment is a compound of Formula (IIc) wherein

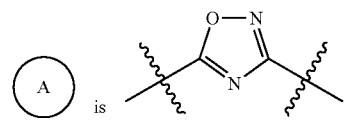

In another embodiment is a compound of Formula (IIc) wherein

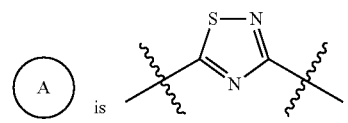

In another embodiment is a compound of Formula (IIc) wherein

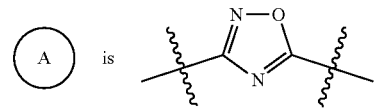

In another embodiment is a compound of Formula (IIc) wherein

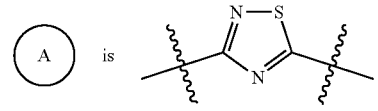

In another embodiment is a compound of Formula (IIc) wherein

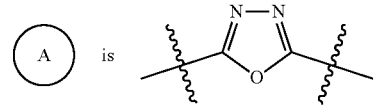

In another embodiment is a compound of Formula (IIc) wherein

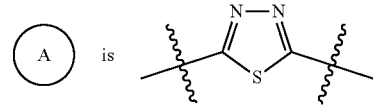

In another embodiment is a compound of Formula (IIc) wherein Z is —O—, —OCH$_2$—, or —CH$_2$O—. In another embodiment is a compound of Formula (IIc) wherein Z is —O—. In another embodiment is a compound of Formula (IIc) wherein Z is —OCH$_2$—. In another embodiment is a compound of Formula (IIc) wherein Z is —CH$_2$O—. In another embodiment is a compound of Formula (IIc) wherein Z is —S—. In another embodiment is a compound of Formula (IIc) wherein Z is —CH$_2$—. In another embodiment is a compound of Formula (IIc) wherein Z is —N(R$_4$)—. In another embodiment is a compound of Formula (IIc) wherein Z is —N(H)—. In another embodiment is a compound of Formula (IIc) wherein Z is —N(CH$_3$)—.

In another embodiment is a compound of Formula (IIc) wherein p is 0. In another embodiment is a compound of Formula (IIc) wherein p is 1.

In some embodiments provided herein, the compound of Formula (II) has the structure of Formula (IId), or a pharmaceutically acceptable salt or solvate thereof:

Formula (IId)

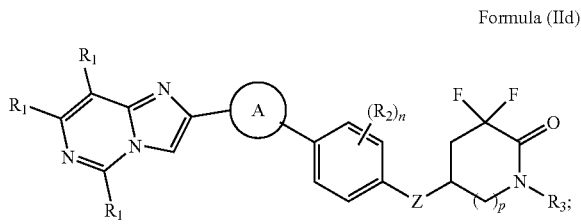

wherein:

is selected from

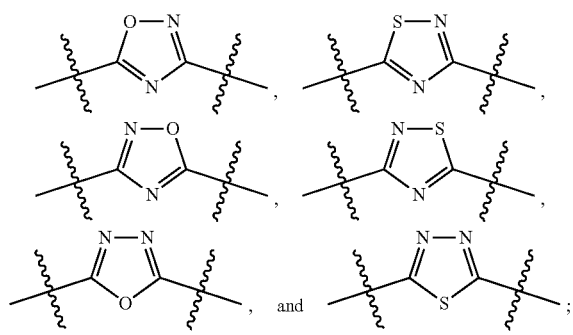

Z is —O—, —S—, —N(R$_4$)—, —CH$_2$—, —OCH$_2$—, or —CH$_2$O—;

each R$_1$ is independently selected from the group consisting of hydrogen, halogen, optionally substituted C$_1$-C$_6$alkyl, optionally substituted C$_2$-C$_6$alkenyl, optionally substituted C$_2$-C$_6$alkynyl, optionally substituted aryl, optionally substituted heteroaryl, optionally substituted C$_3$-C$_8$cycloalkyl, optionally substituted —(C$_1$-C$_2$alkylene)-(C$_3$-C$_8$cycloalkyl), optionally substituted C$_2$-C$_9$heterocycloalkyl, optionally substituted —(C$_1$-C$_2$alkylene)-(C$_2$-C$_9$heterocycloalkyl), optionally substituted —(C$_1$-C$_2$alkylene)-(aryl), optionally substituted —(C$_1$-C$_2$alkylene)-(heteroaryl), —CF$_3$, —OR$_{10}$, —SR$_{10}$, —N(R$_{11}$)R$_{12}$, —N(R$_{11}$)S(O)$_2$R$_{15}$; —N(R$_{13}$)N(R$_{11}$)R$_{12}$, —N(R$_{13}$)N(R$_{11}$)S(O)$_2$R$_{15}$, —C(O)R$_{14}$, —C(O)OR$_{10}$, —C(S)OR$_{10}$, —C(O)SR$_{10}$, —C(O)N(R$_{11}$)R$_{12}$, —C(S)N(R$_{11}$)R$_{12}$, —C(O)N(R$_{11}$)S(O)$_2$R$_{15}$, —C(S)N(R$_{11}$)S(O)$_2$R$_{15}$, —C(O)N(R$_{13}$)N(R$_{11}$)R$_{12}$, —C(S)N(R$_{13}$)N(R$_{11}$)R$_{12}$, and —C(O)N(R$_{13}$)N(R$_{11}$)S(O)$_2$R$_{15}$;

each R$_2$ is independently selected from the group consisting of halogen, optionally substituted C$_1$-C$_6$alkyl, —OR$_{20}$, —SR$_{20}$, —N(R$_{21}$)R$_{22}$, —C(O)R$_{20}$, —C(O)N(R$_{21}$)R$_{22}$, and —N(R$_{23}$)C(O)R$_{20}$;

R$_3$ is selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted heteroaryl, and optionally substituted —(C$_1$-C$_2$alkylene)-(heteroaryl);

R$_4$ is hydrogen or optionally substituted C$_1$-C$_6$alkyl,

R$_{10}$, R$_{13}$ and R$_{14}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{11}$ and R$_{12}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{11}$ and R$_{12}$ together with the nitrogen atom to which they are attached, form an optionally substituted C$_2$-C$_9$heterocycloalkyl ring;

R$_{15}$ is selected from the group consisting of optionally substituted C$_1$-C$_6$alkyl, optionally substituted C$_2$-C$_6$alkenyl, optionally substituted C$_2$-C$_6$alkynyl, optionally substituted C$_3$-C$_8$ cycloalkyl, optionally substituted aryl optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{20}$ and R$_{23}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl);

R$_{21}$ and R$_{22}$ are each independently selected from the group consisting of hydrogen, optionally substituted C$_1$-C$_6$alkyl, optionally substituted C$_2$-C$_6$alkenyl, optionally substituted C$_2$-C$_6$alkynyl, optionally substituted C$_3$-C$_8$cycloalkyl, optionally substituted aryl, optionally substituted —(C$_1$-C$_2$alkylene)-(aryl), optionally substituted C$_2$-C$_9$heterocycloalkyl, optionally substituted heteroaryl, and optionally substituted —(C$_1$-C$_2$alkylene)-(heteroaryl); or optionally R$_{21}$ and R$_{22}$ together with the nitrogen atom to which they are attached, form an optionally substituted C$_2$-C$_9$heterocycloalkyl ring;

n is 0-4; and p is 0 or 1.

In one embodiment is a compound of Formula (IId) wherein each R$_1$ is independently selected from the group consisting of hydrogen, halogen, optionally substituted C$_1$-C$_6$alkyl, —CF$_3$, —OR$_{10}$, —N(R$_{11}$)R$_{12}$, —C(O)R$_{14}$, —C(O)OR$_{10}$, and —C(O)N(R$_{11}$)R$_{12}$. In another embodiment is a compound of Formula (IId) wherein each R$_1$ is independently selected from the group consisting of hydrogen, halogen, optionally substituted C$_1$-C$_6$alkyl, —CF$_3$, —OR$_{10}$, and —N(R$_{11}$)R$_{12}$. In another embodiment is a compound of Formula (IId) wherein each R$_1$ is independently selected from the group consisting of hydrogen, halogen, and —CF$_3$.

In another embodiment is a compound of Formula (IId) wherein n is 3 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (IId) wherein n is 3 and each R$_2$ is independently selected from the group consisting of halogen and optionally substituted C$_1$-C$_6$alkyl. In another embodiment is a compound of Formula (IId) wherein n is 2 and each R$_2$ is independently selected from the group consisting of halogen, optionally substituted C$_1$-C$_6$alkyl, —OR$_{20}$, and —N(R$_{21}$)R$_{22}$. In another embodiment is a compound of Formula (IId) wherein n is 2 and each R$_2$ is independently selected from the group consisting of halogen and optionally substituted C$_1$-C$_6$alkyl. In another embodiment is a compound of Formula (IId) wherein n is 1 and R$_2$ is selected from the group consisting of halogen, optionally substituted C$_1$-C$_6$alkyl, —OR$_{20}$, and —N(R$_{21}$)R$_{22}$. In another embodiment is a compound of Formula (IId) wherein n is 1 and R$_2$ is selected from the group consisting of halogen and optionally substituted C$_1$-C$_6$alkyl. In another embodiment is a compound of Formula (IId) wherein n is 0.

In another embodiment is a compound of Formula (IId) wherein R$_3$ is selected from the group consisting of hydrogen and optionally substituted C$_1$-C$_6$alkyl. In another embodiment is a compound of Formula (IId) wherein R$_3$ is hydrogen. In another embodiment is a compound of Formula (IId) wherein R$_3$ is optionally substituted C$_1$-C$_6$alkyl. In another embodiment is a compound of Formula (IId) wherein R$_3$ is methyl.

In another embodiment is a compound of Formula (IId) wherein

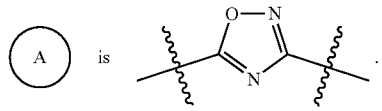

In another embodiment is a compound of Formula (IId) wherein

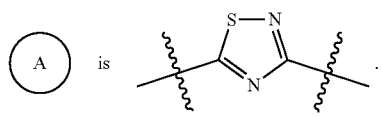

In another embodiment is a compound of Formula (IId) wherein

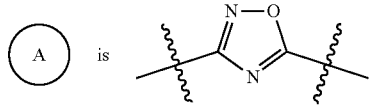

In another embodiment is a compound of Formula (IId) wherein

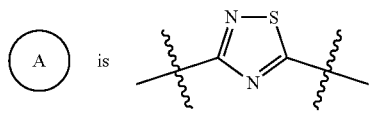

In another embodiment is a compound of Formula (IId) wherein

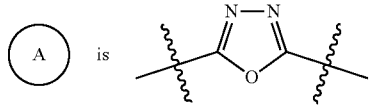

In another embodiment is a compound of Formula (IId) wherein

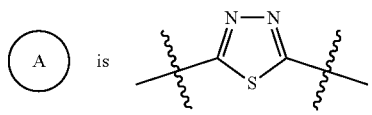

In another embodiment is a compound of Formula (IId) wherein Z is —O—, —OCH$_2$—, or —CH$_2$O—. In another embodiment is a compound of Formula (IId) wherein Z is —O—. In another embodiment is a compound of Formula (IId) wherein Z is —OCH$_2$—. In another embodiment is a compound of Formula (IId) wherein Z is —CH$_2$O—. In another embodiment is a compound of Formula (IId) wherein Z is —S—. In another embodiment is a compound of Formula (IId) wherein Z is —CH$_2$—. In another embodiment is a compound of Formula (IId) wherein Z is —N(R$_4$)—. In another embodiment is a compound of Formula (IId) wherein Z is —N(H)—. In another embodiment is a compound of Formula (IId) wherein Z is —N(CH$_3$)—.

In another embodiment is a compound of Formula (IId) wherein p is 0. In another embodiment is a compound of Formula (IId) wherein p is 1.

In some embodiments provided herein, the compound of Formula (II) has the structure of Formula (IIe), or a pharmaceutically acceptable salt or solvate thereof:

Formula (IIe)

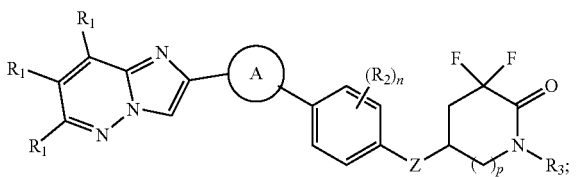

wherein:

is selected from

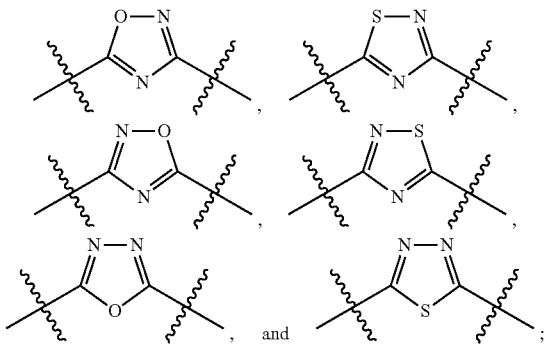

Z is —O—, —S—, —N(R₄)—, —CH₂—, —OCH₂—, or —CH₂O—;

each $R_1$ is independently selected from the group consisting of hydrogen, halogen, optionally substituted $C_1$-$C_6$alkyl, optionally substituted $C_2$-$C_6$alkenyl, optionally substituted $C_2$-$C_6$alkynyl, optionally substituted aryl, optionally substituted heteroaryl, optionally substituted $C_3$-$C_8$cycloalkyl, optionally substituted —($C_1$-$C_2$alkylene)-($C_3$-$C_8$cycloalkyl), optionally substituted $C_2$-$C_9$heterocycloalkyl, optionally substituted —($C_1$-$C_2$alkylene)-($C_2$-$C_9$heterocycloalkyl), optionally substituted —($C_1$-$C_2$alkylene)-(aryl), optionally substituted —($C_1$-$C_2$alkylene)-(heteroaryl), —$CF_3$, —$OR_{10}$, —$SR_{10}$, —$N(R_{11})R_{12}$, —$N(R_{11})S(O)_2R_{15}$; —$N(R_{13})N(R_{11})R_{12}$, —$N(R_{13})N(R_{11})S(O)_2R_{15}$, —$C(O)R_{14}$, —$C(O)OR_{10}$, —$C(S)OR_{10}$, —$C(O)SR_{10}$, —$C(O)N(R_{11})R_{12}$, —$C(S)N(R_{11})R_{12}$, —$C(O)N(R_{11})S(O)_2R_{15}$, —$C(S)N(R_{11})S(O)_2R_{15}$, —$C(O)N(R_{13})N(R_{11})R_{12}$, —$C(S)N(R_{13})N(R_{11})R_{12}$, and —$C(O)N(R_{13})N(R_{11})S(O)_2R_{15}$;

each $R_2$ is independently selected from the group consisting of halogen, optionally substituted $C_1$-$C_6$alkyl, —$OR_{20}$, —$SR_{20}$, —$N(R_{21})R_{22}$, —$C(O)R_{20}$, —$C(O)N(R_{21})R_{22}$, and —$N(R_{23})C(O)R_{20}$;

$R_3$ is selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted heteroaryl, and optionally substituted —($C_1$-$C_2$alkylene)-(heteroaryl);

$R_4$ is hydrogen or optionally substituted $C_1$-$C_6$alkyl, $R_{10}$, $R_{13}$ and $R_{14}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{11}$ and $R_{12}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{11}$ and $R_{12}$ together with the nitrogen atom to which they are attached, form an optionally substituted $C_2$-$C_9$heterocycloalkyl ring;

$R_{15}$ is selected from the group consisting of optionally substituted $C_1$-$C_6$alkyl, optionally substituted $C_2$-$C_6$alkenyl, optionally substituted $C_2$-$C_6$alkynyl, optionally substituted $C_3$-$C_8$ cycloalkyl, optionally substituted aryl optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{20}$ and $R_{23}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl);

$R_{21}$ and $R_{22}$ are each independently selected from the group consisting of hydrogen, optionally substituted $C_1$-$C_6$alkyl, optionally substituted $C_2$-$C_6$alkenyl, optionally substituted $C_2$-$C_6$alkynyl, optionally substituted $C_3$-$C_8$cycloalkyl, optionally substituted aryl, optionally substituted —($C_1$-$C_2$alkylene)-(aryl), optionally substituted $C_2$-$C_9$heterocycloalkyl, optionally substituted heteroaryl, and optionally substituted —($C_1$-$C_2$alkylene)-(heteroaryl); or optionally $R_{21}$ and $R_{22}$ together with the nitrogen atom to which they are attached, form an optionally substituted $C_2$-$C_9$heterocycloalkyl ring;

n is 0-4; and p is 0 or 1.

In one embodiment is a compound of Formula (IIe) wherein each $R_1$ is independently selected from the group consisting of hydrogen, halogen, optionally substituted $C_1$-$C_6$alkyl, —$CF_3$, —$OR_{10}$, —$N(R_{11})R_{12}$, —$C(O)R_{14}$, —$C(O)OR_{10}$, and —$C(O)N(R_{11})R_{12}$. In another embodiment is a compound of Formula (IIe) wherein each $R_1$ is independently selected from the group consisting of hydrogen, halogen, optionally substituted $C_1$-$C_6$alkyl, —$CF_3$, —$OR_{10}$, and —$N(R_{11})R_{12}$. In another embodiment is a compound of Formula (IIe) wherein each $R_1$ is independently selected from the group consisting of hydrogen, halogen, and —$CF_3$.

In another embodiment is a compound of Formula (IIe) wherein n is 3 and each $R_2$ is independently selected from the group consisting of halogen, optionally substituted $C_1$-$C_6$alkyl, —$OR_{20}$, and —$N(R_{21})R_{22}$. In another embodiment is a compound of Formula (IIe) wherein n is 3 and each $R_2$ is independently selected from the group consisting of halogen and optionally substituted $C_1$-$C_6$alkyl. In another embodiment is a compound of Formula (IIe) wherein n is 2 and each $R_2$ is independently selected from the group consisting of halogen, optionally substituted $C_1$-$C_6$alkyl, —$OR_{20}$, and —$N(R_{21})R_{22}$. In another embodiment is a compound of Formula (IIe) wherein n is 2 and each $R_2$ is independently selected from the group consisting of halogen and optionally substituted $C_1$-$C_6$alkyl. In another embodiment is a compound of Formula (IIe) wherein n is 1 and $R_2$ is selected from the group consisting of halogen, optionally substituted $C_1$-$C_6$alkyl, —$OR_{20}$, and —$N(R_{21})R_{22}$. In another embodiment is a compound of Formula (IIe) wherein n is 1 and $R_2$ is selected from the group consisting of halogen and optionally substituted $C_1$-$C_6$alkyl. In another embodiment is a compound of Formula (IIe) wherein n is 0.

In another embodiment is a compound of Formula (IIe) wherein $R_3$ is selected from the group consisting of hydrogen and optionally substituted $C_1$-$C_6$alkyl. In another embodiment is a compound of Formula (IIe) wherein $R_3$ is hydrogen. In another embodiment is a compound of Formula (IIe) wherein $R_3$ is optionally substituted $C_1$-$C_6$alkyl. In another embodiment is a compound of Formula (IIe) wherein $R_3$ is methyl.

In another embodiment is a compound of Formula (IIe) wherein

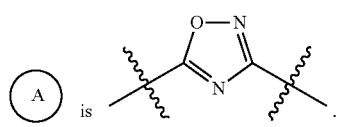

In another embodiment is a compound of Formula (IIe) wherein

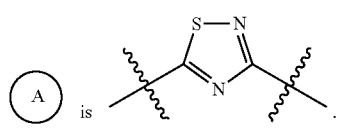

In another embodiment is a compound of Formula (IIe) wherein

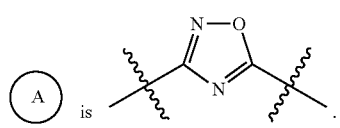

In another embodiment is a compound of Formula (IIe) wherein

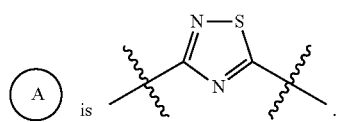

In another embodiment is a compound of Formula (IIe) wherein

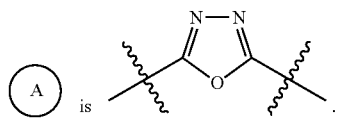

In another embodiment is a compound of Formula (IIe) wherein

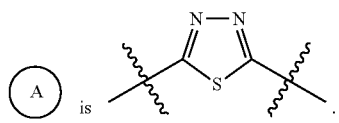

In another embodiment is a compound of Formula (IIe) wherein Z is —O—, —$OCH_2$—, or —$CH_2O$—. In another embodiment is a compound of Formula (IIe) wherein Z is —O—. In another embodiment is a compound of Formula (IIe) wherein Z is —$OCH_2$—. In another embodiment is a compound of Formula (IIe) wherein Z is —$CH_2O$—. In another embodiment is a compound of Formula (IIe) wherein Z is —S—. In another embodiment is a compound of Formula (IIe) wherein Z is —$CH_2$—. In another embodiment is a compound of Formula (IIe) wherein Z is —$N(R_4)$—. In another embodiment is a compound of Formula (IIe) wherein Z is —N(H)—. In another embodiment is a compound of Formula (IIe) wherein Z is —$N(CH_3)$—.

In another embodiment is a compound of Formula (IIe) wherein p is 0. In another embodiment is a compound of Formula (IIe) wherein p is 1.

Any combination of the groups described above for the various variables is contemplated herein. Throughout the specification, groups and substituents thereof can be chosen by one skilled in the field to provide stable moieties and compounds.

In some embodiments is a compound selected from:

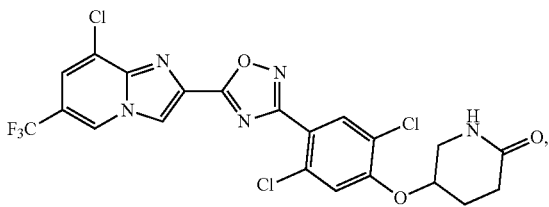

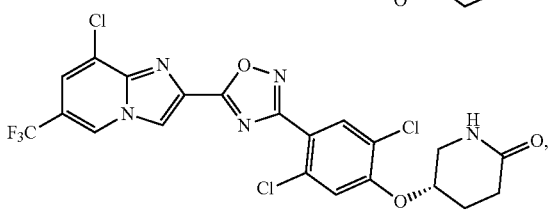

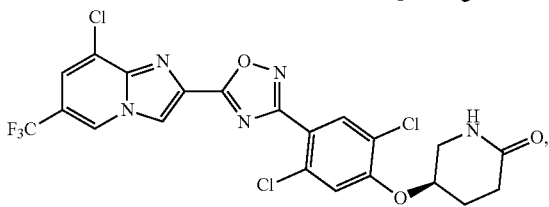

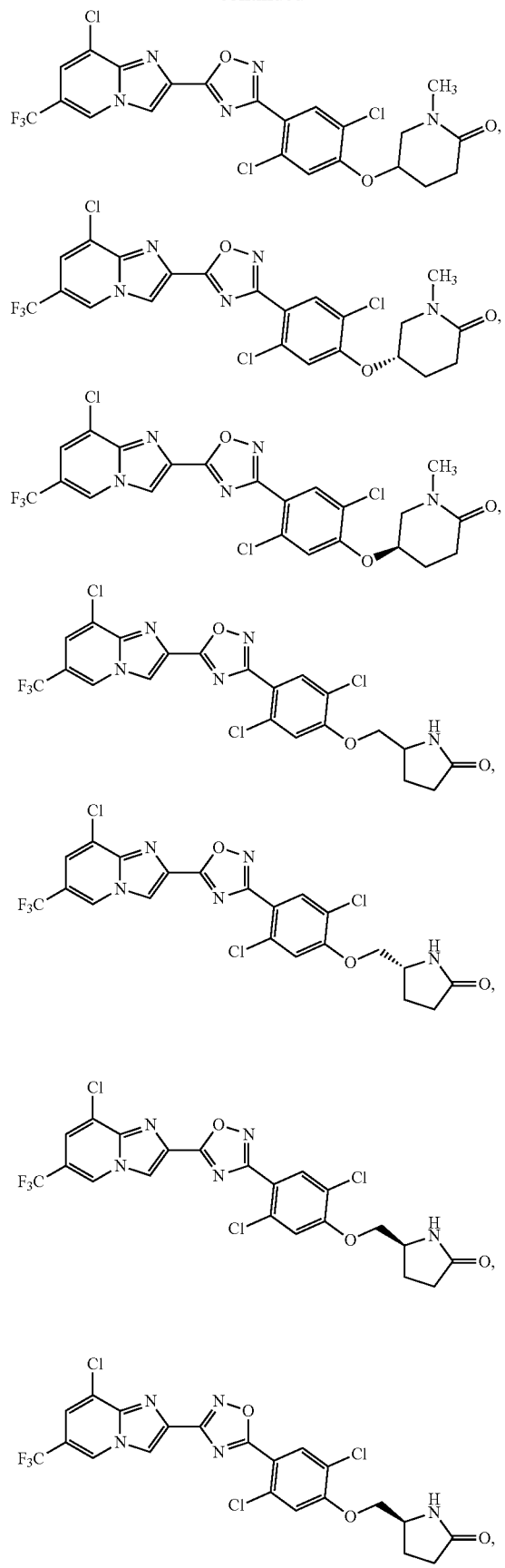
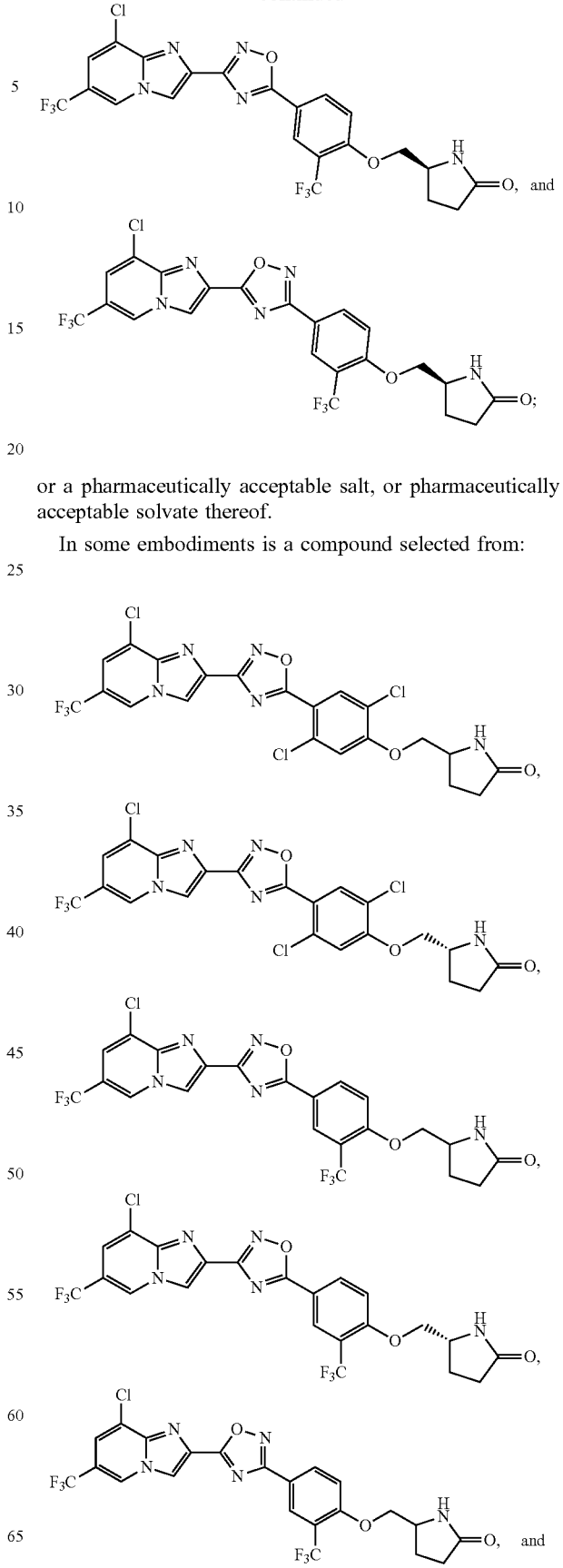
or a pharmaceutically acceptable salt, or pharmaceutically acceptable solvate thereof.
In some embodiments is a compound selected from:

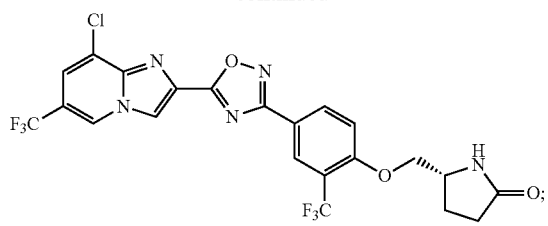
or a pharmaceutically acceptable salt, or pharmaceutically acceptable solvate thereof.
In some embodiments is a compound selected from:
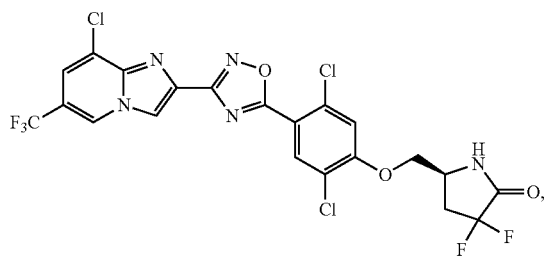
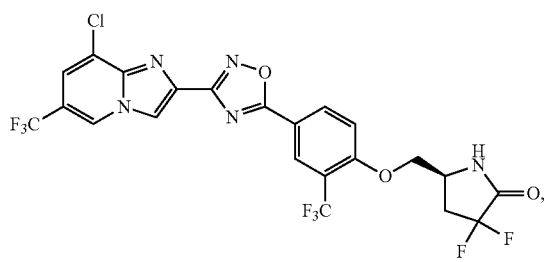
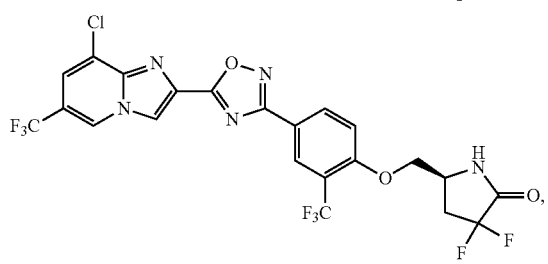
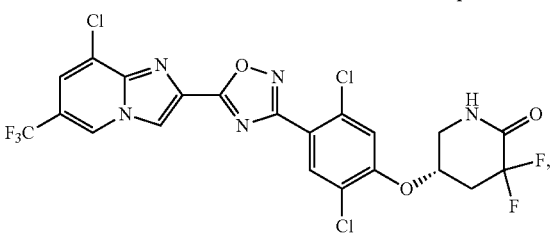
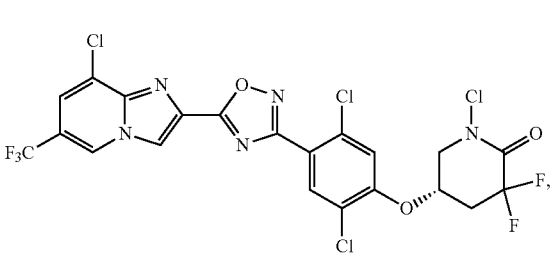
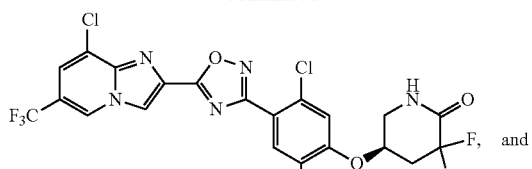
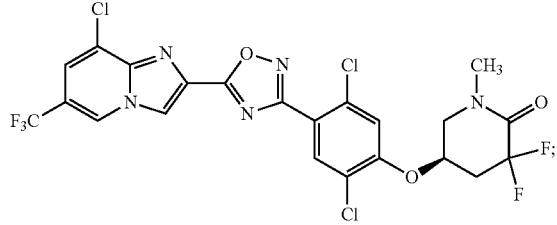
or a pharmaceutically acceptable salt, or pharmaceutically acceptable solvate thereof.
In some embodiments is a compound selected from:
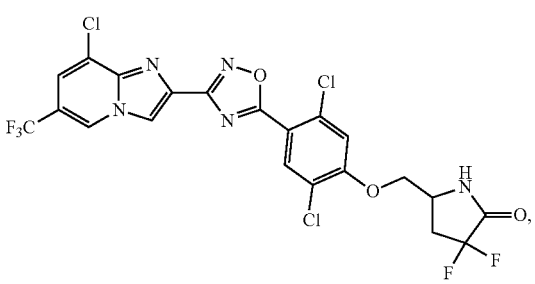
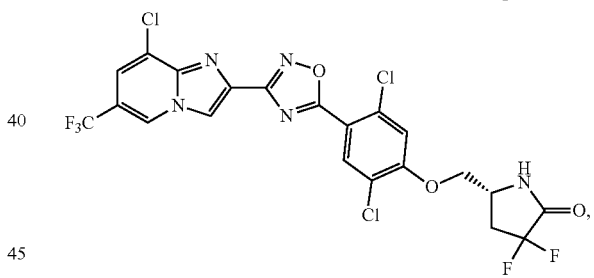
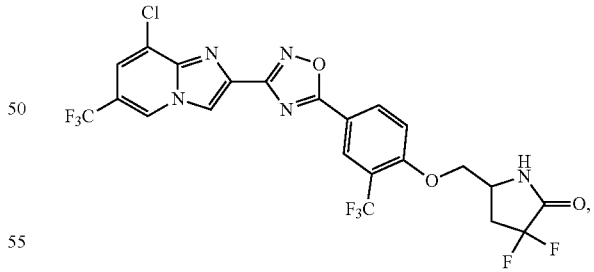
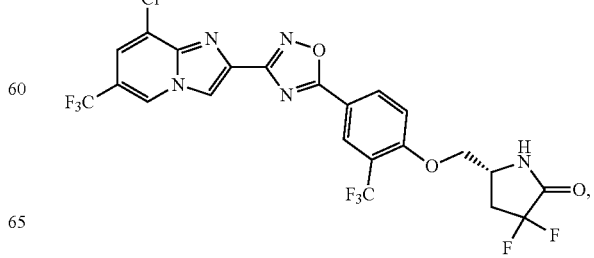

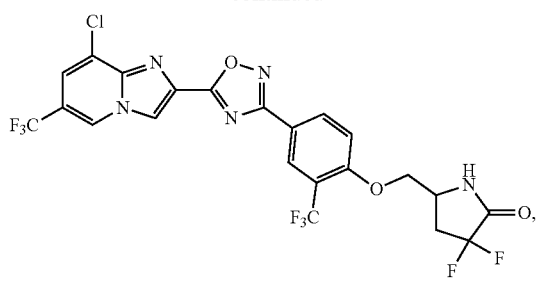
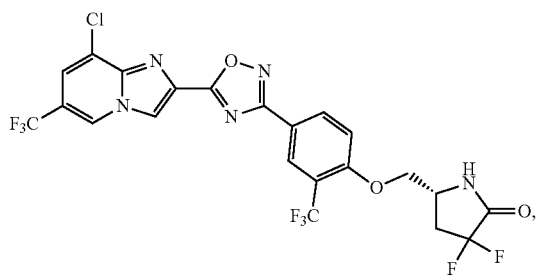
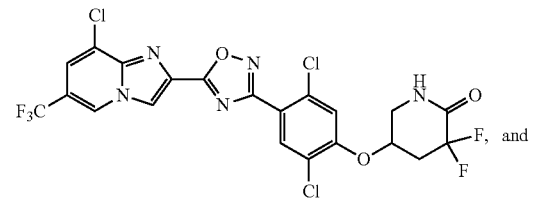
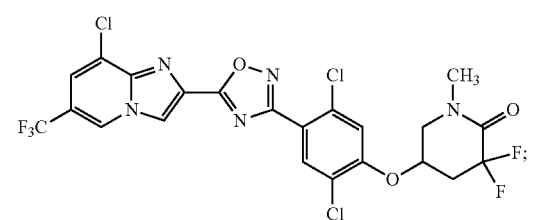
or a pharmaceutically acceptable salt, or pharmaceutically acceptable solvate thereof.
In some embodiments is a compound selected from:
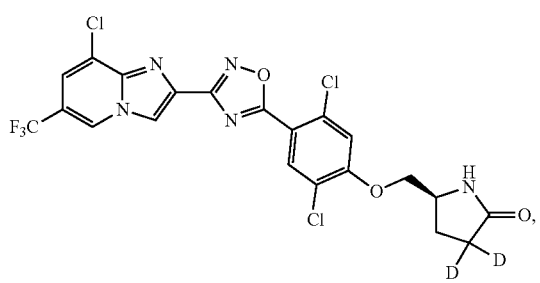
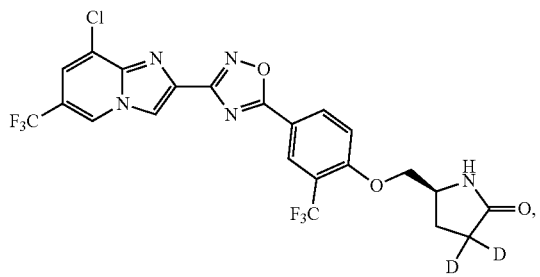
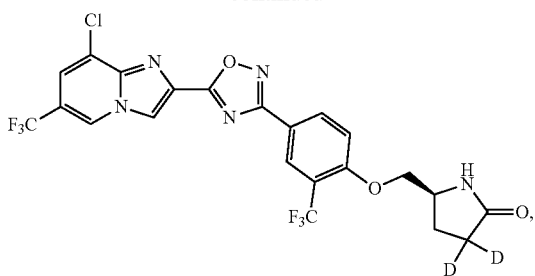
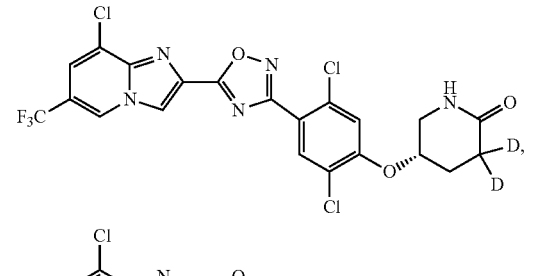
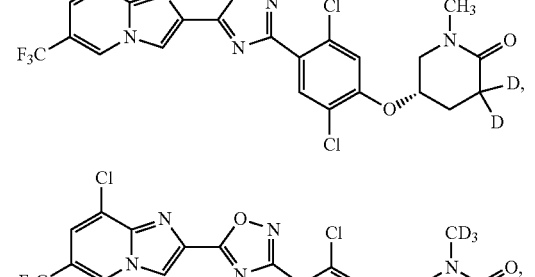
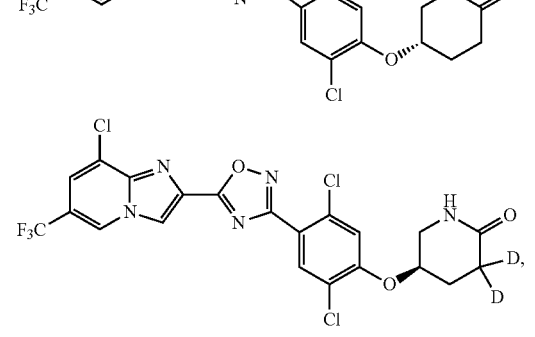
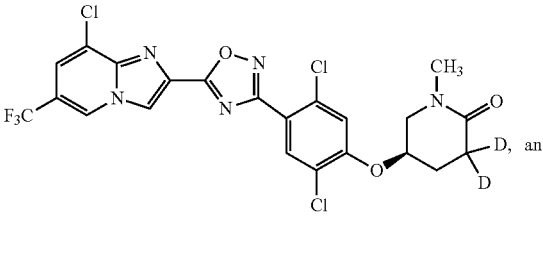
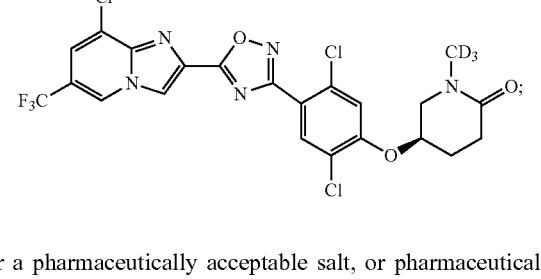
or a pharmaceutically acceptable salt, or pharmaceutically acceptable solvate thereof.

In some embodiments is a compound selected from:

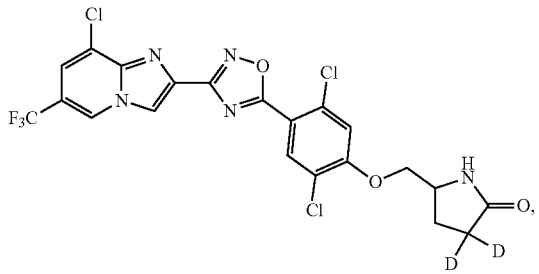

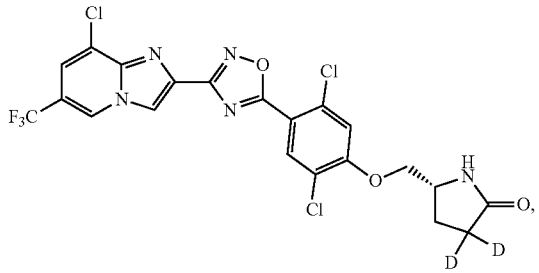

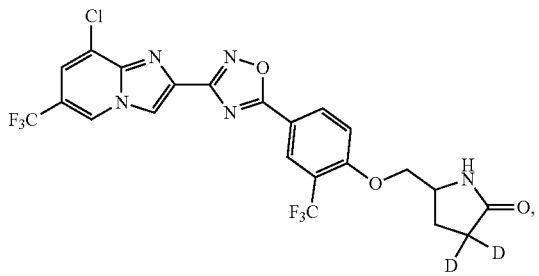

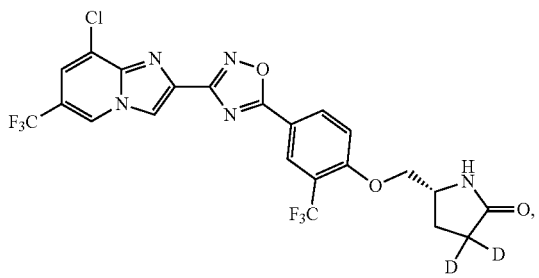

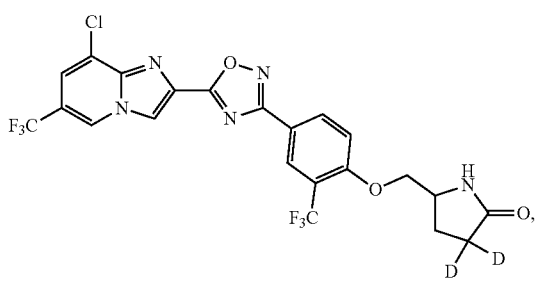

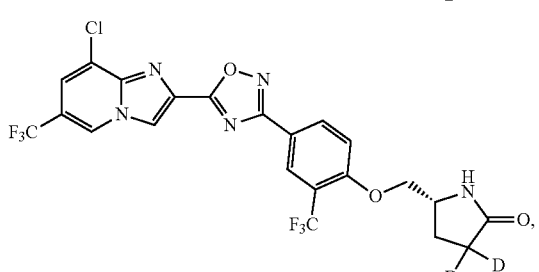

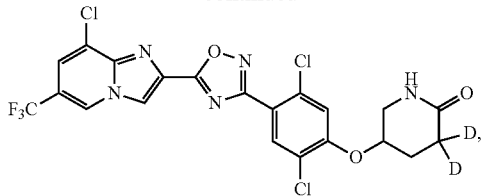

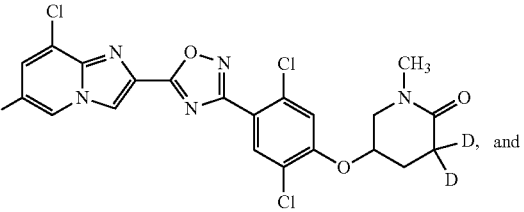

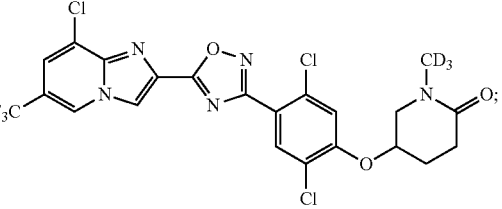

or a pharmaceutically acceptable salt, or pharmaceutically acceptable solvate thereof.

In some embodiments, the therapeutic agent(s) (e.g. compound of Formula (I), (Ia), (Ib), (Ic), (Id), (Ie), (II), (IIa), (IIb), (IIc), (IId), or (IIe)) is present in the pharmaceutical composition as a pharmaceutically acceptable salt. In some embodiments, any compound described above is suitable for any method or composition described herein.

In certain embodiments, the compounds presented herein possess one or more stereocenters and each center independently exists in either the R or S configuration. The compounds presented herein include all diastereomeric, enantiomeric, atropisomers, and epimeric forms as well as the appropriate mixtures thereof. Stereoisomers are obtained, if desired, by methods such as, stereoselective synthesis and/or the separation of stereoisomers by chiral chromatographic columns. In some embodiments, a compound of Formula (I), (Ia), (Ib), (Ic), (Id), (Ie), (II), (IIa), (IIb), (IIc), (IId), or (IIe) is used as a single enantiomer. In some embodiments, a compound of Formula (I), (Ia), (Ib), (Ic), (Id), (Ie), (II), (IIa), (IIb), (IIc), (IId), or (IIe) is used as a racemic mixture. In some embodiments, a compound of Formula (I), (Ia), (Ib), (Ic), (Id), (Ie), (II), (IIa), (IIb), (IIc), (IId), or (IIe) possesses hindered rotation about a single bond resulting in atropisomers.

The methods and formulations described herein include the use of N-oxides (if appropriate), crystalline forms (also known as polymorphs), or pharmaceutically acceptable salts of compounds having the structures presented herein, as well as active metabolites of these compounds having the same type of activity.

In some situations, compounds may exist as tautomers. All tautomers are included within the scope of the compounds presented herein.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like.

Prodrug forms of the herein described compounds, wherein the prodrug is metabolized in vivo to produce a compound of Formula (I), (Ia), (Ib), (Ic), (Id), (Ie), (II), (IIa), (IIb), (IIc), (IId), or (IIe), as set forth herein are included within the scope of the claims. In some cases, some of the herein-described compounds may be a prodrug for another derivative or active compound.

In specific embodiments, the compounds described herein exist in solvated forms with pharmaceutically acceptable solvents such as water, ethanol, and the like. In other embodiments, the compounds described herein exist in unsolvated form.

In some embodiments, the compounds of Formula (I), (Ia), (Ib), (Ic), (Id), (Ie), (II), (IIa), (IIb), (IIc), (IId), or (IIe) described herein include solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol.

In some embodiments, sites on the compounds of Formula (I), (Ia), (Ib), (Ic), (Id), (Ie), (II), (IIa), (IIb), (IIc), (IId), or (IIe) disclosed herein are susceptible to various metabolic reactions. Therefore incorporation of appropriate substituents at the places of metabolic reactions will reduce, minimize or eliminate the metabolic pathways. In specific embodiments, the appropriate substituent to decrease or eliminate the susceptibility of the aromatic ring to metabolic reactions is, by way of example only, a halogen, deuterium or an alkyl group.

In some embodiments, the compounds of Formula (I), (Ia), (Ib), (Ic), (Id), (Ie), (II), (IIa), (IIb), (IIc), (IId), or (IIe) disclosed herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

In some embodiments, compounds described herein, such as compounds of Formula (I), (Ia), (Ib), (Ic), (Id), (Ie), (II), (IIa), (IIb), (IIc), (IId), or (IIe), are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen to provide stable moieties and compounds.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics. In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

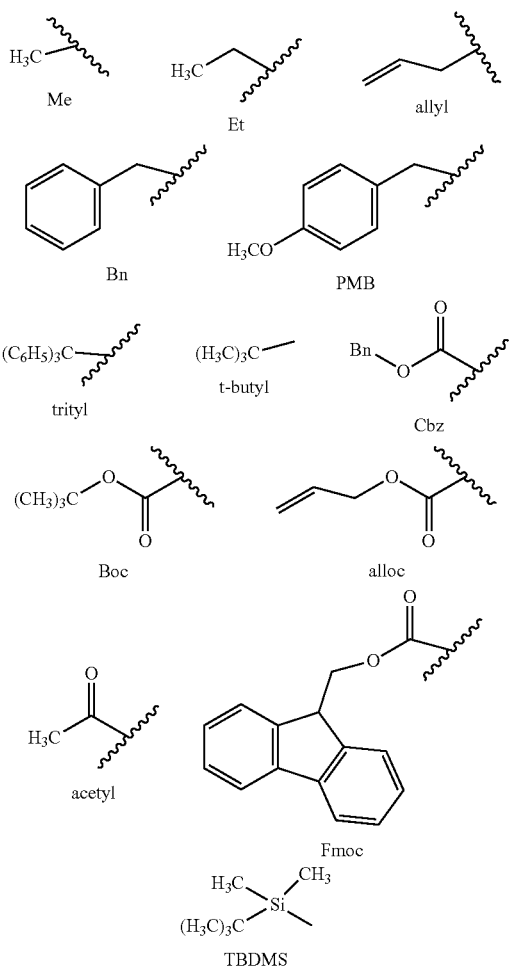

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Certain Terminology

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ . . . $C_1$-$C_x$. $C_1$-$C_x$ refers to the number of carbon atoms that make up the moiety to which it designates (excluding optional substituents).

An "alkyl" group refers to an aliphatic hydrocarbon group. The alkyl groups may or may not include units of unsaturation. The alkyl moiety may be a "saturated alkyl" group, which means that it does not contain any units of unsaturation (i.e. a carbon-carbon double bond or a carbon-carbon triple bond). The alkyl group may also be an "unsaturated alkyl" moiety, which means that it contains at least one unit of unsaturation. The alkyl moiety, whether saturated or unsaturated, may be branched, straight chain, or cyclic.

The "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, hexyl, propen-3-yl (allyl), cyclopropylmethyl, cyclobutylmethyl, cyclopentylmethyl, cyclohexylmethyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a type of alkyl group in which two atoms of the alkyl group form a double bond that is not part of an aromatic group. Non-limiting examples of an alkenyl group include —CH=$CH_2$, —C($CH_3$)=$CH_2$, —CH=$CHCH_3$, —CH=C($CH_3$)$_2$ and —C($CH_3$)=$CHCH_3$. The alkenyl moiety may be branched, straight chain, or cyclic (in which case, it would also be known as a "cycloalkenyl" group). Alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a type of alkyl group in which the two atoms of the alkyl group form a triple bond. Non-limiting examples of an alkynyl group include —C≡CH, —C≡$CCH_3$, —C≡$CCH_2CH_3$ and —C≡$CCH_2CH_2CH_3$. The "R" portion of the alkynyl moiety may be branched, straight chain, or cyclic. An alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —$NH_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —$CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

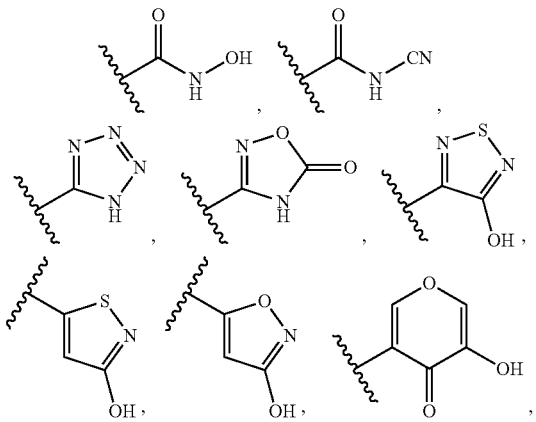

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Illustrative examples of cycloalkyl groups include, but are not limited to, the following moieties:

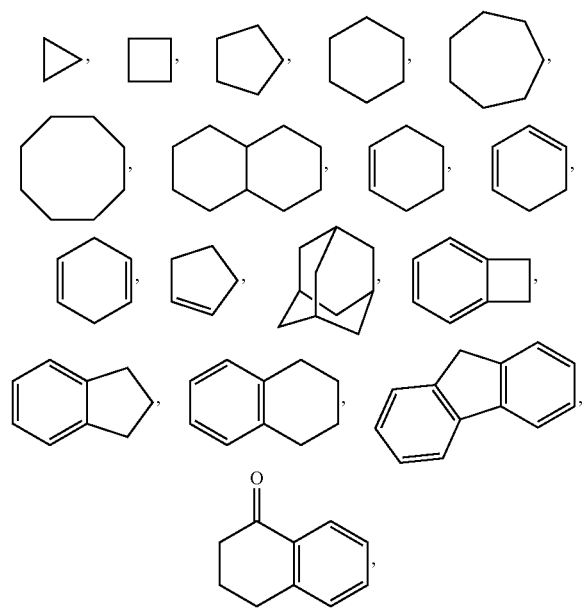

and the like.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Polycyclic heteroaryl groups may be fused or non-fused. Illustrative examples of heteroaryl groups include the following moieties:

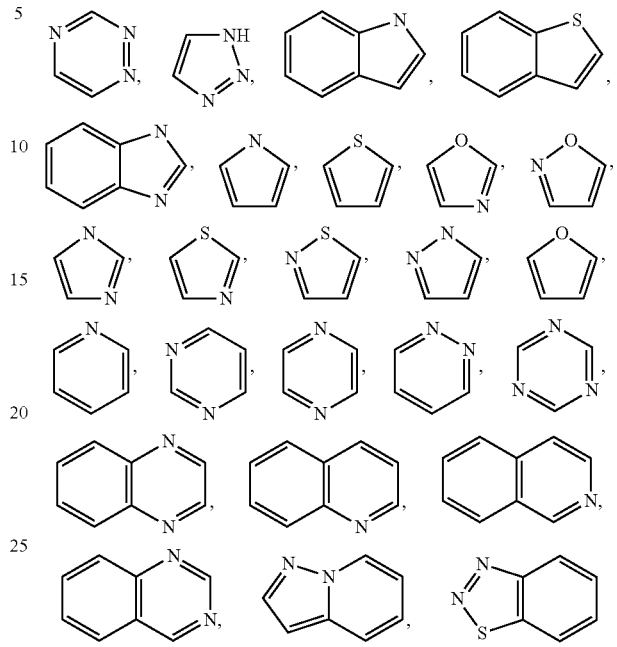

and the like.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. Illustrative examples of heterocycloalkyl groups, also referred to as non-aromatic heterocycles, include:

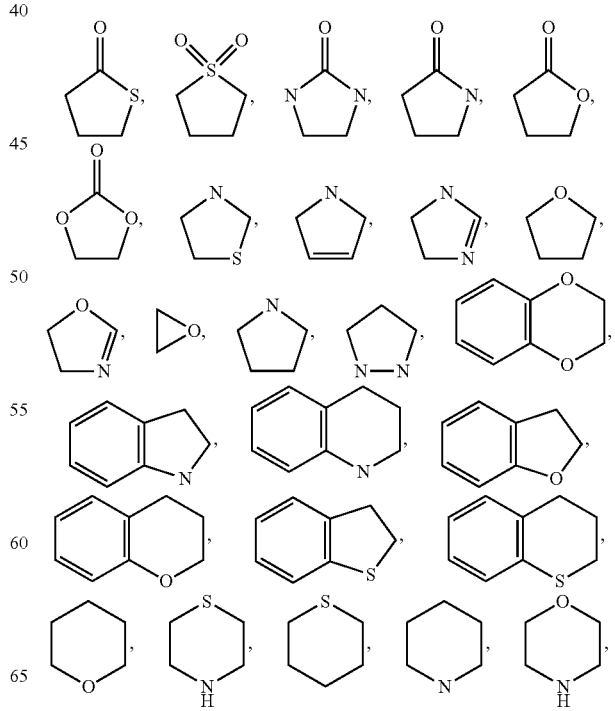

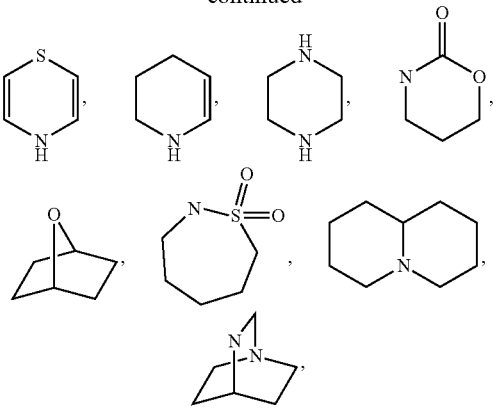

and the like. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, —$CF(CH_3)_2$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —$CH_2$—NH—$OCH_3$, $CH_2$—O—Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and $CH_2$—O—Si($CH_3$)$_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. $NH_2$, —NHR, —N(R)$_2$), and the protected derivatives thereof. In some embodiments, optional substituents are independently selected from halogen, —CN, —$NH_2$, —NH($CH_3$), —N($CH_3$)$_2$, —OH, —$CO_2H$, —$CO_2$alkyl, —C(=O)$NH_2$, —C(=O)NH(alkyl), —C(=O)N(alkyl)$_2$, —S(=O)$_2NH_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some embodiments, optional substituents are independently selected from halogen, —CN, —$NH_2$, —OH, —NH($CH_3$), —N($CH_3$)$_2$, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The methods and formulations described herein include the use of crystalline forms (also known as polymorphs), or pharmaceutically acceptable salts of compounds having the structure of Formula (I), (Ia), (Ib), (Ic), (Id), (Ie), (II), (IIa), (IIb), (IIc), (IId), or (IIe), as well as active metabolites of these compounds having the same type of activity.

As used herein, the term "about" or "approximately" means within 20%, preferably within 10%, and more preferably within 5% of a given value or range.

The term a "therapeutically effective amount" as used herein refers to the amount of an S1P receptor modulator that, when administered to a mammal in need, is effective to at least partially ameliorate or to at least partially prevent diseases, disorders or conditions described herein.

As used herein, the term "expression" includes the process by which polynucleotides are transcribed into mRNA and translated into peptides, polypeptides, or proteins.

The term "activator" is used in this specification to denote any molecular species that results in activation of the indicated receptor, regardless of whether the species itself binds to the receptor or a metabolite of the species binds to the receptor. Thus, the activator can be a ligand of the receptor or it can be an activator that is metabolized to the ligand of the receptor, i.e., a metabolite that is formed in tissue and is the actual ligand.

The term "antagonist" as used herein, refers to a small-molecule agent that binds to a receptor and subsequently decreases the agonist induced transcriptional activity of the receptor.

The term "agonist" as used herein, refers to a small-molecule agent that binds to a receptor and subsequently increases receptor transcriptional activity in the absence of a known agonist.

The term "inverse agonist" as used herein, refers to a small-molecule agent that binds to a receptor and subsequently decreases the basal level of receptor transcriptional activity that is present in the absence of a known agonist.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "S1P receptor modulator" includes S1P receptor agonists, partial agonists, antagonists and tissue selective S1P receptor modulators.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. Those skilled in the art recognize that a therapy which reduces the severity of a pathology in one species of mammal is predictive of the effect of the therapy on another species of mammal.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions and Methods of Administration of S1P Receptor Modulators Administration of S1P receptor modulators as described herein can be in any pharmacological form including a therapeutically effective amount of an S1P receptor modulator alone or in combination with a pharmaceutically acceptable carrier.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (Ia), (Ib), (Ic), (Id), (Ie), (II), (IIa), (IIb), (IIc), (IId), or (IIe) described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors.

In another aspect, provided herein is a pharmaceutical composition comprising a compound of Formula (I), (Ia), (Ib), (Ic), (Id), (Ie), (II), (IIa), (IIb), (IIc), (IId), or (IIe), or a pharmaceutically acceptable salt or solvate thereof, and a pharmaceutically acceptable diluent, excipient or binder. In one embodiment, the pharmaceutical composition comprising the compound of Formula (I), (Ia), (Ib), (Ic), (Id), (Ie), (II), (IIa), (IIb), (IIc), (IId), or (IIe), or a pharmaceutically acceptable salt or solvate thereof, is formulated for a route of administration selected from oral administration, parenteral administration, buccal administration, nasal administration, topical administration, or rectal administration.

In another aspect is a method of treating a disease, disorder or condition in a mammal that would benefit from S1P receptor modulation comprising administering to the mammal a therapeutically effective amount of a compound of Formula (I), (Ia), (Ib), (Ic), (Id), (Ie), (II), (IIa), (IIb), (IIc), (IId), or (IIe), or a pharmaceutically acceptable salt or solvate thereof.

In another embodiment is a method of treating a disease, disorder or condition in a mammal that would benefit from S1P receptor modulation comprising administering to the mammal a therapeutically effective amount of a compound of Formula (I), (Ia), (Ib), (Ic), (Id), (Ie), (II), (IIa), (IIb), (IIc), (IId), or (IIe), or a pharmaceutically acceptable salt or solvate thereof; wherein the disease, disorder or condition in a mammal is selected from multiple sclerosis, ulcerative colitis, and Crohn's disease. In another embodiment is a method of treating a disease, disorder or condition in a mammal that would benefit from S1P receptor modulation comprising administering to the mammal a therapeutically effective amount of a compound of Formula (I), (Ia), (Ib), (Ic), (Id), (Ie), (II), (IIa), (IIb), (IIc), (IId), or (IIe), or a pharmaceutically acceptable salt or solvate thereof; wherein the disease, disorder or condition in a mammal is multiple sclerosis. In another embodiment is a method of treating a disease, disorder or condition in a mammal that would benefit from S1P receptor modulation comprising administering to the mammal a therapeutically effective amount of a compound of Formula (I), (Ia), (Ib), (Ic), (Id), (Ie), (II), (IIa), (IIb), (IIc), (IId), or (IIe), or a pharmaceutically acceptable salt or solvate thereof; wherein the disease, disorder or condition in a mammal is ulcerative colitis. In another embodiment is a method of treating a disease, disorder or condition in a mammal that would benefit from S1P receptor modulation comprising administering to the mammal a therapeutically effective amount of a compound of Formula (I), (Ia), (Ib), (Ic), (Id), (Ie), (II), (IIa), (IIb), (IIc), (IId), or (IIe), or a pharmaceutically acceptable salt or solvate thereof; wherein the disease, disorder or condition in a mammal is Crohn's disease.

In a further embodiment is a method of treating a disease, disorder or condition in a mammal that would benefit from S1P receptor modulation comprising administering to the mammal a therapeutically effective amount of a compound of Formula (I), (Ia), (Ib), (Ic), (Id), (Ie), (II), (IIa), (IIb), (IIc), (IId), or (IIe), or a pharmaceutically acceptable salt or solvate thereof; wherein the disease, disorder or condition in a mammal is rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

In some embodiments a compound of Formula (I), (Ia), (Ib), (Ic), (Id), (Ie), (II), (IIa), (IIb), (IIc), (IId), or (IIe) is used singly or in combination with one or more therapeutic agents as components of mixtures (as in combination therapy). In some embodiments a compound of Formula (I), (Ia), (Ib), (Ic), (Id), (Ie), (II), (IIa), (IIb), (IIc), (IId), or (IIe) is used singly. In some embodiments a compound of Formula (I), (Ia), (Ib), (Ic), (Id), (Ie), (II), (IIa), (IIb), (IIc), (IId), or (IIe) is used in combination with another S1P receptor modulator or another type of therapeutic agent, or both. In some embodiments a compound of Formula (I), (Ia), (Ib), (Ic), (Id), (Ie), (II), (IIa), (IIb), (IIc), (IId), or (IIe) is used in combination with another S1P receptor modulator. In some embodiments a compound of Formula (I), (Ia), (Ib), (Ic), (Id), (Ie), (II), (IIa), (IIb), (IIc), (IId), or (IIe) is used in combination with another type of therapeutic agent. In some embodiments a compound of Formula (I), (Ia), (Ib), (Ic), (Id), (Ie), (II), (IIa), (IIb), (IIc), (IId), or (IIe) is used in combination with another S1P receptor modulator and another type of therapeutic agent.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound of Formula (I), (Ia), (Ib), (Ic), (Id), (Ie), (II), (IIa), (IIb), (IIc), (IId), or (IIe) described herein, can be formulated into any suitable dosage form, including but not limited to, aqueous oral dispersions, liquids, gels, syrups, elixirs, slurries, suspensions, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the S1P receptor modulator and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the S1P receptor modulator activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such S1P receptor modulators can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. S1P receptor modulators that exhibit large therapeutic indices are preferred. While S1P receptor modulators that exhibit toxic side effects may be used, care should be taken to design a delivery system that targets such modulators to the site of affected tissue in order to minimize potential damage to uninfected cells and, thereby, reduce side effects.

The data obtained from the cell culture assays and animal studies can be used in formulating a range of dosage for use in humans. The dosage of such S1P receptor modulators lies preferably within a range of circulating concentrations that include the $ED_{50}$ with little or no toxicity. The dosage may vary within this range depending upon the dosage form employed and the route of administration utilized. For any S1P receptor modulator used in a method described herein, the therapeutically effective dose can be estimated initially from cell culture assays. A dose may be formulated in animal models to achieve a circulating plasma concentration range that includes the $IC_{50}$ (i.e., the concentration of the S1P receptor modulator that achieves a half-maximal inhibition of symptoms) as determined in cell culture. Such information can be used to more accurately determine useful doses in humans. Levels in plasma may be measured, for example, by high performance liquid chromatography.

Methods of Dosing and Treatment Regimens

The compounds described herein can be used in the preparation of medicaments for the modulation of the S1P receptor, or for the treatment of diseases or conditions that would benefit, at least in part, from modulation of the S1P receptor. In addition, a method for treating any of the diseases or conditions described herein in a subject in need of such treatment, involves administration of pharmaceutical compositions containing at least one compound described herein, or a pharmaceutically acceptable salt, or pharmaceutically acceptable solvate or hydrate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.01 mg per day to about 5000 mg per day, in some embodiments, about 1 mg per day to about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.001 mg/kg to about 30 mg/kg. In one embodiment, the daily dosages are from about 0.01 mg/kg to about 10 mg/kg. An indicated daily dosage in the larger mammal, including, but not limited to, humans, is in the range from about 0.1 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeu-

EXAMPLES

The following examples are offered for purposes of illustration, and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1: Synthesis of (S)-5-((2,5-dichloro-4-(5-(8-chloro-6-(trifluoromethyl)imidazo[1,2-a]pyridin-2-yl)-1,2,4-oxadiazol-3-yl)phenoxy)methyl)pyrrolidin-2-one (11)

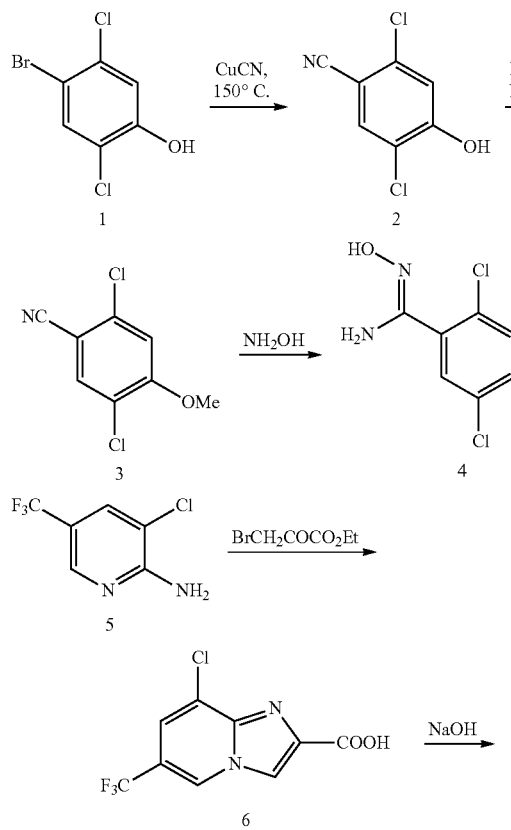

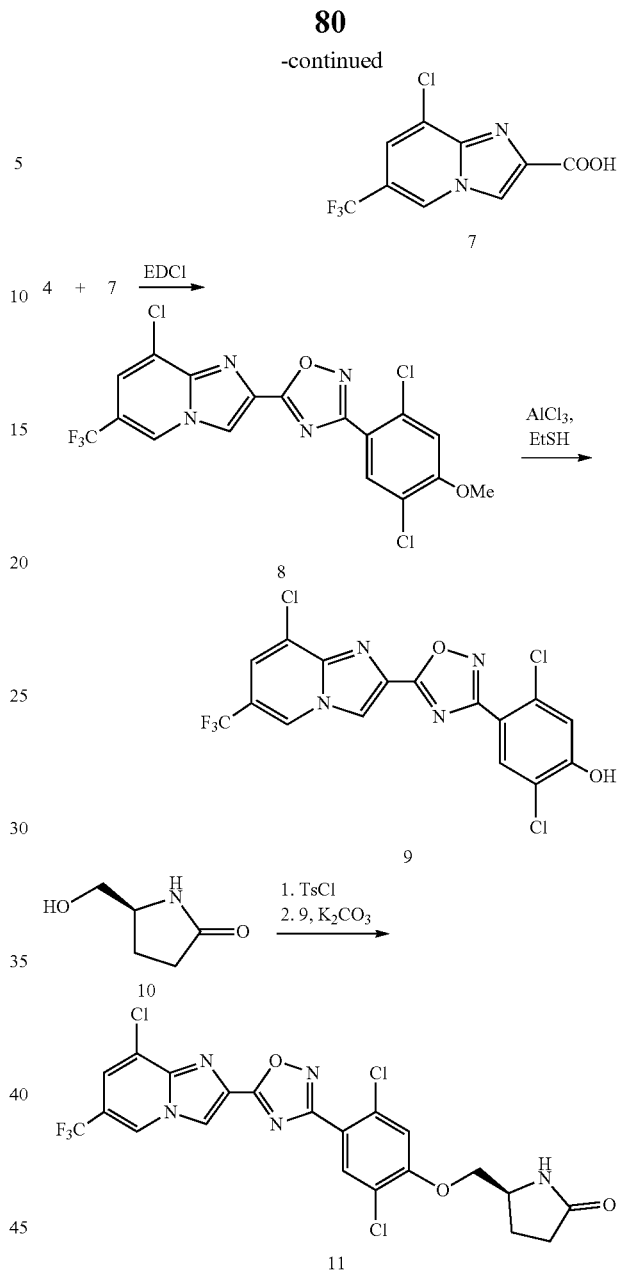

To a stirred solution of 2,5-dichloro-4-bromophenol (1) (210.0 g, 0.86 mol) in DMF (1000 mL) was added cuprous cyanide (101.5 g, 1.13 mmol) at room temperature. The reaction mixture was stirred at 150° C. for 4 h. The mixture was concentrated under vacuum. Water and EtOAc were added to the residue and then filtered through a pad of celite. The filtrate was extracted with EtOAc and the combined organic layers were dried over anhydrous $Na_2SO_4$ and concentrated under vacuum. The residue was recrystallized from petroleum ether/EtOAc (10:1, 1400 mL) to afford 2,5-dichloro-4-hydroxybenzonitrile (2) (93.0 g, 57%) as a white solid.

To a stirred solution of 2,5-dichloro-4-hydroxybenzonitrile (2) (35.0 g, 186 mmol) in DMF (150 mL) was added NaH (13.7 g, 347 mmol) in small portions at 0° C. and the mixture was stirred for 30 min at 0° C. Methyl iodide (35 mL, 560 mmol) was added dropwise and the reaction mixture was allowed to warm to room temperature and stirred for 3 h. The mixture was cooled to 0° C. and ice-water was added carefully. The resulting precipitate was collected by filtration, washed with water and dried to afford compound (3) (29 g, 78%) as a white solid.

To a stirred solution of hydroxylamine hydrochloride (3) (64.0 g, 0.5 mol) in EtOH (500 mL) was added triethylamine (160.0 g, 1.27 mol) and the mixture was stirred for 30 min at room temperature. Compound 2 was added and the reaction mixture was stirred at 80° C. for 4 h. The mixture was concentrated and the residue was dissolved in EtOAc. The resulting solution was washed with water, dried over anhydrous $Na_2SO_4$ and concentrated under vacuum to afford a mixture (60.0 g, compound (4) and 2,5-dichloro-4-methoxybenzamide, 1:2) as an off-white solid. The solid was slurried in MBTE and then filtered. The filtrate was concentrated under vacuum to afford a solid (40.1 g, 28%, compound (4) and 2,5-dichloro-4-methoxybenzamide, 1:1).

To a stirred solution of 2-amino-3-chloro-5-trifluoromethylpyridine (5) (50.0 g, 0.25 mmol) in EtOH (500 mL) was added ethylbromopyruvate (80.0 mL, 0.64 mol) at room temperature. The reaction mixture was heated at 80° C. for 48 h and then cooled to room temperature. The mixture was concentrated and the residue was suspended in diethyl ether. The resulting precipitate was collected by filtration and dried under vacuum to afford ethyl 8-chloro-6-(trifluoromethyl) imidazo[1,2-c]pyridine-2-carboxylate (6) (64.0 g, 86%) as an off-white solid.

To a stirred solution of ethyl 8-chloro-6-(trifluoromethyl) imidazo[1,2-c]pyridine-2-carboxylate (6) (64.0 g, 0.22 mol) in MeOH (64.0 mL) was added 1M aqueous NaOH (640.0 mL). The reaction mixture was heated at 50° C. for 1 h and then cooled to room temperature. The mixture was concentrated under vacuum. Water was added to the residue and the mixture was acidified to pH=4 with AcOH. The resulting precipitate was collected by filtration, washed with water and dried under vacuum to afford compound (7) (24.0 g) as an off-white solid. The filtrate was extracted with EtOAc and the combined organic layers were dried over anhydrous $Na_2SO_4$ and concentrated under vacuum to afford another portion of compound (7) (20.0 g) as an off-white solid (combined yield 77%).

To a stirred solution of compound (7) (26.5 g, 100 mmol) in DMF (50.0 mL) were added EDCI-HCl (19.2 g, 100 mmol) and HOBt (13.5 g, 100 mmol). The mixture was stirred for 15 min and hydroxyimidate (4) (36 g, 54% purity, 100 mmol) was added. The reaction mixture was stirred at 100° C. for 12 h. The mixture was concentrated under vacuum and the residue was purified by flash column chromatography on silica gel (petroleum ether/EtOAc=10:1) to afford compound (8) (12.6 g, 33%) as a white solid.

To a cold solution of compound (8) (16 g, 34.5 mmol) in DCM (110 mL) was added $AlCl_3$ (23 g, 172.5 mmol) in small portions under $N_2$ maintaining the temperature below 10° C. The light brown suspension was stirred for 10 min and then EtSH (12.8 mL, 172.5 mmol) was added dropwise maintaining the temperature below 5° C. The reaction mixture was stirred for 2.5 h at below 10° C. and then slowly poured into ice-water with strong agitation. The organic layer was separated and the aqueous layer was extracted with DCM. The combined DCM layers were washed with water, dried over anhydrous $Na_2SO_4$ and concentrated. The residue was azeotroped with toluene to afford compound (9) (15.5 g, 100%) as an off-white solid.

To a solution of (S)-5-(hydroxymethyl)-2-pyrrolidinone (10) (420 mg, 3.65 mmol) and p-toluenesulfonyl chloride (696 mg, 3.65 mmol) in DCM (20 mL) were added DMAP (446 mg, 3.65 mmol) and $Et_3N$ (369 mg, 3.65 mmol) at 0° C. The reaction mixture was allowed to warm to room temperature and stirred overnight. The reaction was quenched with 20 mL of water and the aqueous layer was extracted with DCM. The combined organic extracts were washed with 1N aqueous HCl, dried over anhydrous $Na_2SO_4$ and concentrated under vacuum. The residue was recrystallized from petroleum ether/DCM (20:1, 30 mL) to afford (S)-(5-oxopyrrolidin-2-yl)methyl 4-methylbenzenesulfonate (700 mg, 71%) as a white solid.

To a solution of compound (9) (300 mg, 0.67 mmol) and (S)-(5-oxopyrrolidin-2-yl)methyl 4-methylbenzenesulfonate (199 mg, 0.74 mmol) in acetonitrile (25 mL) was added potassium carbonate (185 mg, 1.34 mmol). The reaction mixture was heated at 76° C. for 13 h and then cooled to room temperature. The mixture was diluted with water (20 mL) and extracted with DCM (25 mL×2). The combined organic phases were washed with brine, dried over anhydrous $Na_2SO_4$ and concentrated under vacuum. The residue was purified by flash column chromatography on silica gel and then recrystallized from EtOAc to give compound (11) (30 mg, 8%). $^1$H NMR (400 MHz, DMSO-$d_6$) δ 9.33 (s, 1H), 9.08 (s, 1H), 8.12 (s, 1H), 8.07 (s, 1H), 7.82 (s, 1H), 7.56 (s, 1H), 4.20-4.18 (m, 2H), 3.97-3.95 (m, 1H), 2.44-2.33 (m, 1H), 2.27-2.12 (m, 2H), 1.99-1.96 (m, 1H). LC-MS (ESI): m/z calcd for $C_{21}H_{13}Cl_3F_3N_5O_3$ 545.00, found: 546.73 [M+H]$^+$.

Example 2: Synthesis of (R)-5-((2,5-dichloro-4-(5-(8-chloro-6-(trifluoromethyl)imidazo[1,2-a]pyridin-2-yl)-1,2,4-oxadiazol-3-yl)phenoxy)methyl)pyrrolidin-2-one (13)

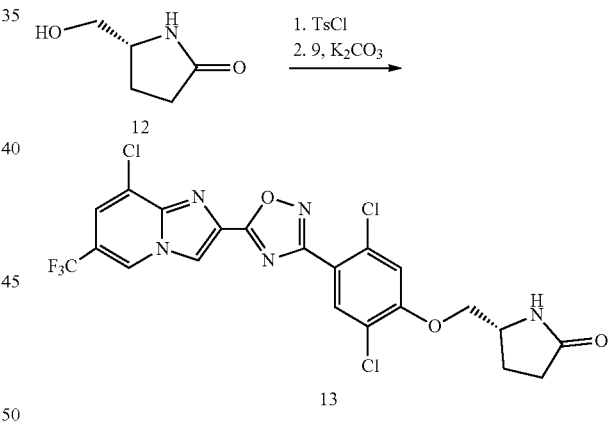

To a solution of (R)-5-(hydroxymethyl)-2-pyrrolidinone (12) (320 mg, 2.78 mmol) and p-toluenesulfonyl chloride (530 mg, 2.78 mmol) in DCM (20 mL) were added DMAP (339 mg, 2.78 mmol) and $Et_3N$ (280 mg, 2.78 mmol) at 0° C. The reaction mixture was allowed to warm to room temperature and stirred overnight. The reaction was quenched with 20 mL of water and the aqueous layer was extracted with DCM. The combined organic extracts were washed with 1N aqueous HCl, dried over anhydrous $Na_2SO_4$ and concentrated under vacuum. The residue was recrystallized from petroleum ether/DCM (20:1, 25 mL) to afford (R)-(5-oxopyrrolidin-2-yl)methyl 4-methylbenzenesulfonate (400 mg, yield 53.4%) as a white solid.

To a solution of compound (9) (300 mg, 0.67 mmol) and (R)-(5-oxopyrrolidin-2-yl)methyl 4-methylbenzenesulfonate (199 mg, 0.74 mmol) in acetonitrile (25 mL) was added potassium carbonate (185 mg, 1.34 mmol). The reaction mixture was heated at 76° C. for 13 h and then cooled to room temperature. The mixture was diluted with water (20 mL) and extracted with DCM (25 mL×2). The combined organic phases were washed with brine, dried over anhydrous $Na_2SO_4$ and concentrated under vacuum. The residue was purified by flash column chromatography on silica gel and then recrystallized from EtOAc to give compound (13) (40.3 mg, 11%). $^1H$ NMR (400 MHz, DMSO-$d_6$): δ 9.33 (s, 1H), 9.07 (s, 1H), 8.12 (s, 1H), 8.07 (s, 1H), 7.81 (s, 1H), 7.56 (s, 1H), 4.22-4.16 (m, 2H), 3.98-3.95 (m, 1H), 2.41-2.33 (m, 1H), 2.29-2.16 (m, 2H), 1.99-1.96 (m, 1H). LC-MS (ESI): m/z calcd for $C_{21}H_{13}Cl_3F_3N_5O_3$ 545.00, found: 546.58 [M+H]$^+$.

Example 3: Synthesis of (R)-5-((2,5-dichloro-4-(5-(8-chloro-6-(trifluoromethyl)imidazo[1,2-a]pyridin-2-yl)-1,2,4-oxadiazol-3-yl)phenoxy)methyl)pyrrolidin-2-one (15)

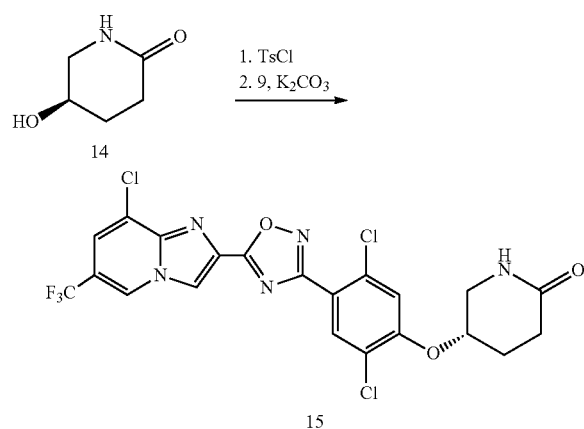

To a solution of (R)-5-hydroxypiperidin-2-one (14) (500 mg, 4.34 mmol) and p-toluenesulfonyl chloride (827 mg, 4.34 mmol) in DCM (20 mL) were added DMAP (530 mg, 4.34 mmol) and $Et_3N$ (438 mg, 4.34 mmol) at 0° C. The reaction mixture was allowed to warm to room temperature and stirred overnight. The reaction was quenched with 20 mL of water and the aqueous layer was extracted with DCM. The combined organic extracts were washed with 1N aqueous HCl, dried over anhydrous $Na_2SO_4$ and concentrated under vacuum. The residue was recrystallized from petroleum ether/DCM (20:1, 30 mL) to afford (R)-6-oxopiperidin-3-yl 4-methylbenzenesulfonate (670 mg, yield 57%) as a white solid.

To a solution of compound (9) (750 mg, 1.67 mmol) and (R)-6-oxopiperidin-3-yl 4-methylbenzenesulfonate (450 mg, 1.67 mmol) in acetonitrile (40 mL) was added potassium carbonate (461 mg, 3.34 mmol). The reaction mixture was heated at 76° C. for 18 h and then cooled to room temperature. The mixture was diluted with water (50 mL) and extracted with DCM (45 mL×2). The combined organic phases were washed with brine, dried over anhydrous $Na_2SO_4$ and concentrated under vacuum. The residue was purified by flash column chromatography on silica gel and then recrystallized from EtOAc to give compound (15) (130 mg, yield 14%). $^1H$ NMR (400 MHz, DMSO-$d_6$): δ 9.33 (s, 1H), 9.07 (s, 1H), 8.12 (s, 1H), 8.07 (s, 1H), 7.73 (s, 1H), 7.47 (s, 1H), 5.17-5.15 (m, 1H), 3.53-3.49 (m, 1H), 3.39-3.34 (m, 1H), 2.36-2.21 (m, 2H), 2.12-2.08 (m, 2H). LC-MS (ESI): m/z calcd for $C_{21}H_{13}Cl_3F_3N_5O_3$: 545.00, found: 546.65 [M+H]$^+$.

Example 4: Synthesis of (S)-5-(2,5-dichloro-4-(5-(8-chloro-6-(trifluoromethyl)imidazo[1,2-a]pyridin-2-yl)-1,2,4-oxadiazol-3-yl)phenoxy)-1-methylpiperidin-2-one (16)

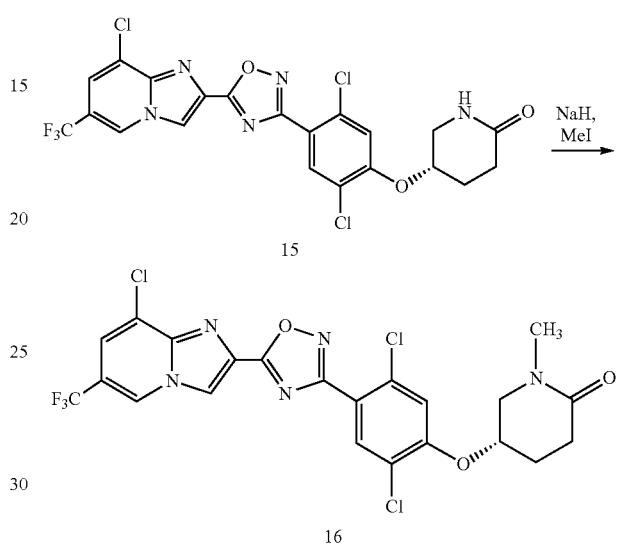

To a solution of compound (15) (100 mg, 0.18 mmol) in THF (75 mL) was added NaH (15 mg, 0.37 mmol) at 0° C. and the mixture was stirred for 30 min at 0° C. Methyl iodide (129 mg, 0.91 mmol) was added dropwise and the reaction mixture was allowed to warm to room temperature and stirred for 3 h. The mixture was cooled to 0° C. and ice-water was added carefully. The resulting mixture was extracted with EtOAc. The combined extracts were washed with brine, dried over anhydrous $Na_2SO_4$ and concentrated under vacuum. The residue was purified by flash column chromatography on silica gel and then recrystallized from EtOAc to give compound (16) (21.7 mg, 21%). $^1H$ NMR (400 MHz, DMSO-$d_6$): δ 9.33 (s, 1H), 9.07 (s, 1H), 8.12 (s, 1H), 8.08 (s, 1H), 7.75 (s, 1H), 5.21 (s, 1H), 3.72-3.67 (m, 1H), 3.50-3.46 (m, 1H), 2.83 (s, 3H), 2.43-2.29 (m, 2H), 2.11 (m, 2H). LC-MS (ESI): m/z calcd for $C_{22}H_{15}Cl_3F_3N_5O_3$: 559.02, found: 560.55 [M+H]$^+$.

Example 5: Synthesis of (R)-5-(2,5-dichloro-4-(5-(8-chloro-6-(trifluoromethyl)imidazo[1,2-a]pyridin-2-yl)-1,2,4-oxadiazol-3-yl)phenoxy)piperidin-2-one (18)

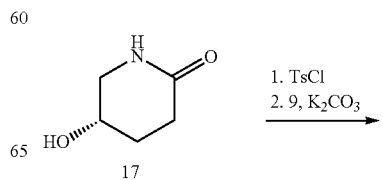

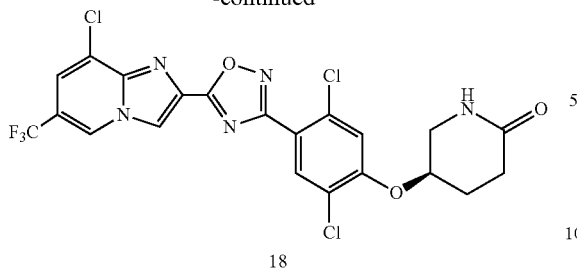

18

To a solution of (S)-5-hydroxypiperidin-2-one (500 mg, 4.34 mmol) and p-toluenesulfonyl chloride (17) (827 mg, 4.34 mmol) in DCM (20 mL) were added DMAP (530 mg, 4.34 mmol) and Et$_3$N (438 mg, 4.34 mmol) at 0° C. The reaction mixture was allowed to warm to room temperature and stirred overnight. The reaction was quenched with 20 mL of water and the aqueous layer was extracted with DCM. The combined organic extracts were washed with 1N aqueous HCl, dried over anhydrous Na$_2$SO$_4$ and concentrated under vacuum. The residue was recrystallized from petroleum ether/DCM (20:1, 30 mL) to afford (S)-6-oxopiperidin-3-yl 4-methylbenzenesulfonate (700 mg, 60%) as a white solid.

To a solution of compound (9) (750 mg, 1.67 mmol) and (S)-6-oxopiperidin-3-yl 4-methylbenzenesulfonate (450 mg, 1.67 mmol) in acetonitrile (40 mL) was added potassium carbonate (461 mg, 3.34 mmol). The reaction mixture was heated at 76° C. for 18 h and then cooled to room temperature. The mixture was diluted with water (50 mL) and extracted with DCM (45 mL×2). The combined organic phases were washed with brine, dried over anhydrous Na$_2$SO$_4$ and concentrated under vacuum. The residue was purified by flash column chromatography on silica gel and then recrystallized from EtOAc to give compound (18) (134 mg, yield 15%). $^1$H NMR (400 MHz, DMSO-d$_6$) δ 9.33 (s, 1H), 9.07 (s, 1H), 8.12 (s, 1H), 8.08 (s, 1H), 7.74 (s, 1H), 7.48 (s, 1H), 5.17-5.15 (m, 1H), 3.53-3.49 (m, 1H), 3.39-3.34 (m, 1H), 2.36-2.22 (m, 2H), 2.11-2.08 (m, 2H). LC-MS (ESI): m/z calcd for C$_{21}$H$_{13}$Cl$_3$F$_3$N$_5$O$_3$: 545.00, found: 546.51 [M+H]$^+$.

Example 6: Synthesis of (R)-5-(2,5-dichloro-4-(5-(8-chloro-6-(trifluoromethyl)imidazo[1,2-a]pyridin-2-yl)-1,2,4-oxadiazol-3-yl)phenoxy)-1-methylpiperidin-2-one (19)

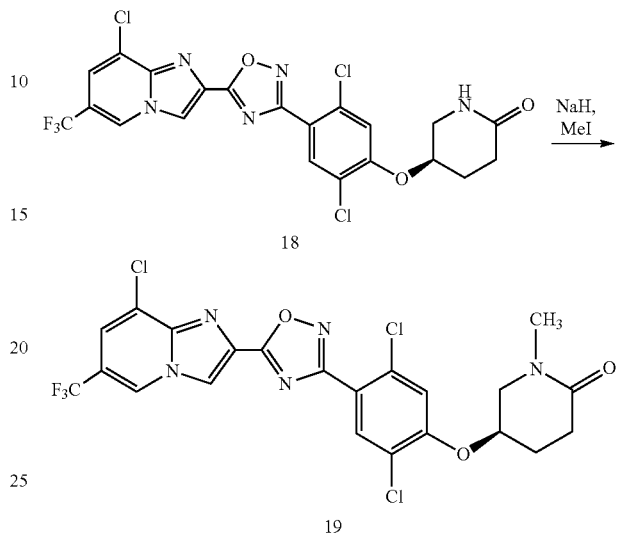

To a solution of compound (18) (100 mg, 0.18 mmol) in THF (75 mL) was added NaH (15 mg, 0.37 mmol) at 0° C. and the mixture was stirred for 30 min at 0° C. Methyl iodide (129 mg, 0.91 mmol) was added dropwise and the reaction mixture was allowed to warm to room temperature and stirred for 3 h. The mixture was cooled to 0° C. and ice-water was added carefully. The mixture was extracted with EtOAc. The combined extracts were washed with brine, dried over anhydrous Na$_2$SO$_4$ and concentrated under vacuum. The residue was purified by flash column chromatography on silica gel and then recrystallized from EtOAc to give compound (19) (27.7 mg, 27%). $^1$H NMR (400 MHz, DMSO-d$_6$) δ 9.34 (s, 1H), 9.07 (s, 1H), 8.13 (s, 1H), 8.09 (s, 1H), 7.76 (s, 1H), 5.22 (m, 1H), 3.71-3.67 (m, 1H), 3.50-3.46 (m, 1H), 2.83 (s, 3H), 2.43-2.28 (m, 2H), 2.11 (m, 2H). LC-MS (ESI): m/z calcd for C$_{22}$H$_{15}$C$_{13}$F$_3$N$_5$O$_3$: 559.02, found: 560.47 [M+H]$^+$.

Examples 7-9

The following compounds were prepared in a similar manner as described above.

| Example | Structure | LCMS (ESI) m/z |
|---|---|---|
| 7 | 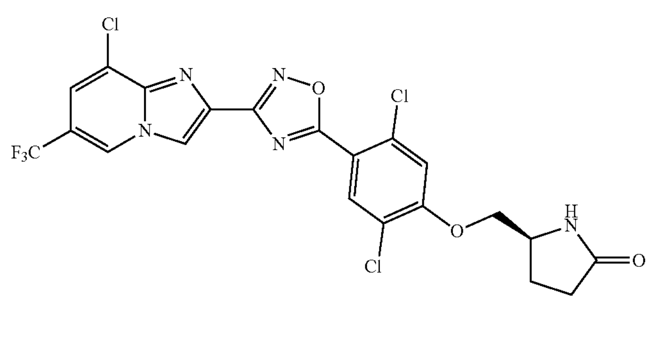 [SMILES: O=C1CC[C@@H](COc2cc(Cl)c(-c3nc(-c4cn5cc(C(F)(F)F)cc(Cl)c5n4)no3)cc2Cl)N1] | 546.3 |

| Example | Structure | LCMS (ESI) m/z |
|---|---|---|
| 8 | 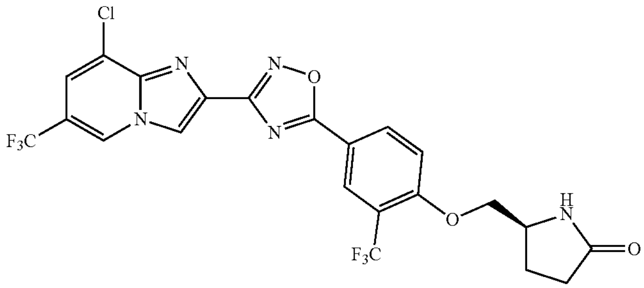 [SMILES: O=C1CC[C@@H](COc2ccc(-c3nc(-c4cn5cc(C(F)(F)F)cc(Cl)c5n4)no3)cc2C(F)(F)F)N1] | 546.50 |
| 9 | 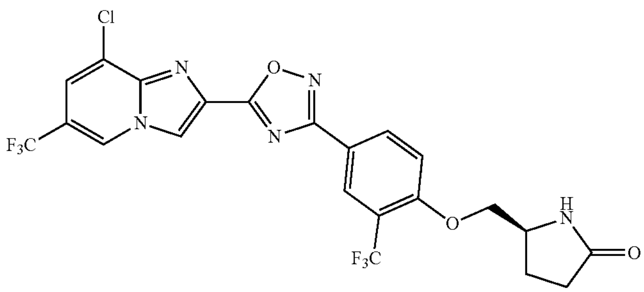 [SMILES: O=C1CC[C@@H](COc2ccc(-c3noc(-c4cn5cc(C(F)(F)F)cc(Cl)c5n4)n3)cc2C(F)(F)F)N1] | 546.73 |

Examples 10-16

The following compounds are prepared in a similar manner as described above.

| Example | Structure |
|---|---|
| 10 | 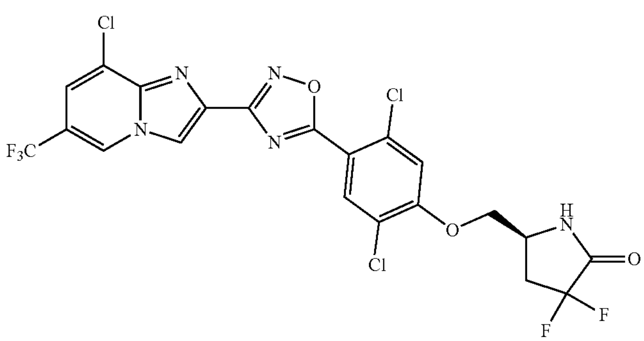 [SMILES: O=C1N[C@H](COc2cc(Cl)c(-c3nc(-c4cn5cc(C(F)(F)F)cc(Cl)c5n4)no3)cc2Cl)CC1(F)F] |
| 11 | 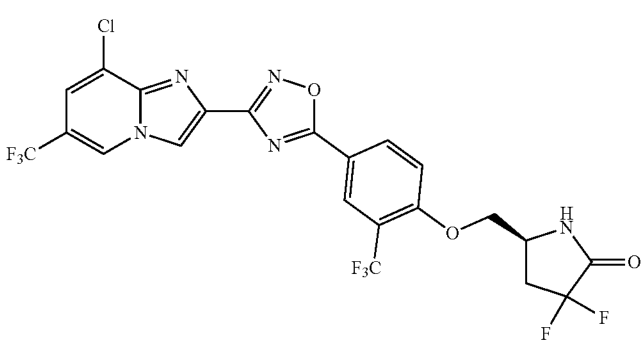 [SMILES: O=C1N[C@H](COc2ccc(-c3nc(-c4cn5cc(C(F)(F)F)cc(Cl)c5n4)no3)cc2C(F)(F)F)CC1(F)F] |

| Example | Structure |
|---|---|
| 12 | 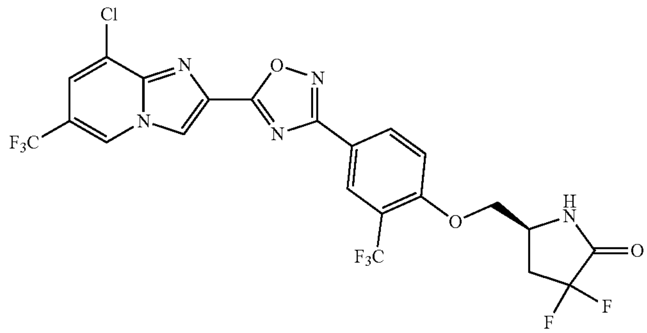 [SMILES: O=C1N[C@H](COc2ccc(-c3noc(-c4cn5cc(C(F)(F)F)cc(Cl)c5n4)n3)cc2C(F)(F)F)CC1(F)F] |
| 13 | 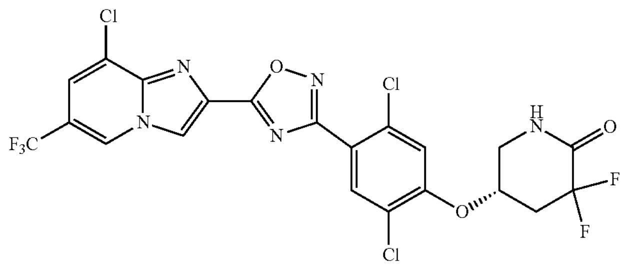 [SMILES: O=C1NC[C@@H](Oc2cc(Cl)c(-c3noc(-c4cn5cc(C(F)(F)F)cc(Cl)c5n4)n3)cc2Cl)CC1(F)F] |
| 14 | 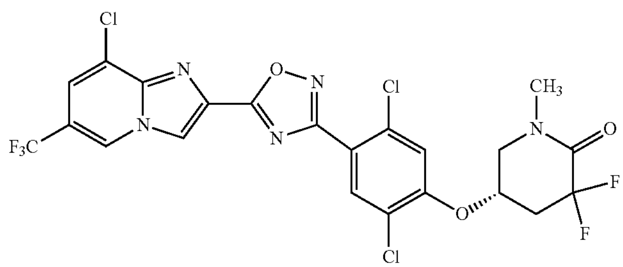 [SMILES: CN1C[C@@H](Oc2cc(Cl)c(-c3noc(-c4cn5cc(C(F)(F)F)cc(Cl)c5n4)n3)cc2Cl)CC(F)(F)C1=O] |
| 15 | 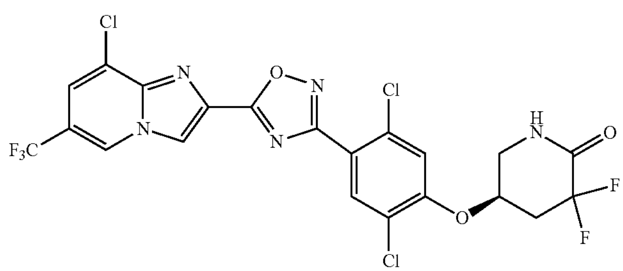 [SMILES: O=C1NC[C@H](Oc2cc(Cl)c(-c3noc(-c4cn5cc(C(F)(F)F)cc(Cl)c5n4)n3)cc2Cl)CC1(F)F] |
| 16 | 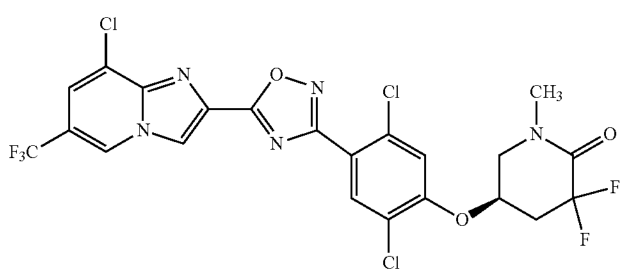 [SMILES: CN1C[C@H](Oc2cc(Cl)c(-c3noc(-c4cn5cc(C(F)(F)F)cc(Cl)c5n4)n3)cc2Cl)CC(F)(F)C1=O] |

Example 17: GTPγS Binding Assay

S1P1 membrane is prepared from CHO-K1 Gαqi5 cells expression full-length human S1P1. Scintillation proximity assay (SPA) is performed by incubating membranes, GTPγ$^{35}$S, and compounds at various concentrations for 60 minutes. Wheat germ agglutinin-coated SPA beads are added and incubated for 60 minutes before centrifugation and scintillation counting. $EC_{50}$ data for exemplified compounds is shown below in Table 1.

TABLE 1

| Example | EC$_{50}$ (µM) |
|---|---|
| 1 | A |
| 5 | A |
| 6 | A |

A = EC$_{50}$ < 1 µM

Example 18: Ca$^{2+}$ Flux Assay

Cells were rapidly thawed by removing from liquid nitrogen and immediately immersing in a 37° C. water bath. Immediately after ice thawed, the exterior of the exterior of the vial was sterilized with 70% ethanol. 1 mL of pre-warmed Media Component was added to each vial of cells. The contents from two vials were placed into a 15 mL conical tube and the volume was brought to 10 mL of Media Component. The cell suspension was centrifuged at 190×g for four minutes. The supernatant was removed and 10.5 mL of pre-warmed Media Component was added to resuspend the cell pellet. The cell suspension was seeded into the appropriate assay microplate (100 µL/well for 96-well plate, 25 µL/well for 384-well plate). When seeding was complete, the assay plate was kept at room temperature for 30 minutes and then moved to a humidified 37° C. 5% CO$_2$ incubator for 24 hours. After 24 hour incubation, the assay plate was removed from the incubator and washed sufficiently with Hank's Balanced Salt Solution (HBSS) supplemented with 20 mM HEPES, 2.5 mM Probenecid at pH 7.4 to remove all trace of Media Component. Fluo-8, AM (AAT Bioquest: 21080) Ca$^{2+}$ dye was prepared by dissolving 1 mg of Fluo-8 NW in 200 µL of DMSO. Once dissolved, 10 µL of Fluo-8 NW Ca$^{2+}$ dye solution was placed into 10 mL of HBSS 20 mM HEPES, 2.5 mM Probenecid pH 7.4 buffer and applied to assay microplate (Ca$^{2+}$ dye at 10 µL/10 mL is sufficient for loading one (1) microplate). FLIPR was set up to dispense 3× ligand to appropriate wells in the assay plate. The excitation wavelength was set at 470-495 nm (FLIPRTETRA) or 485 nm (FLIPR1, FLIPR2, FLIPR3) and emission wavelength at 515-565 nm (FLIPRTETRA) or emission filter for Ca2+ dyes (FLIPR1, FLIPR2, FLIPR3). The pipet tip height was set to 5 µL below liquid level and dispense rate to 75 µL/sec (96-well format) or 50 µL/sec (384-well format). The plate layout and tip layout was set for each individual experiment. The time course was set for 180 seconds, with ligand addition at 10 seconds. The ligands were prepared in non-binding surface Corning plates (Corning 3605—96-well or Corning 3574—384-well). After the run was complete, negative control correction was applied and data analyzed utilizing the maximum statistic. As shown in FIG. 1, a compound of Formula (I) described herein, showed cellular potency in the assay (EC50~200 nM).

Example 19: Pk Study and Lymphocyte Count

Figure 2:
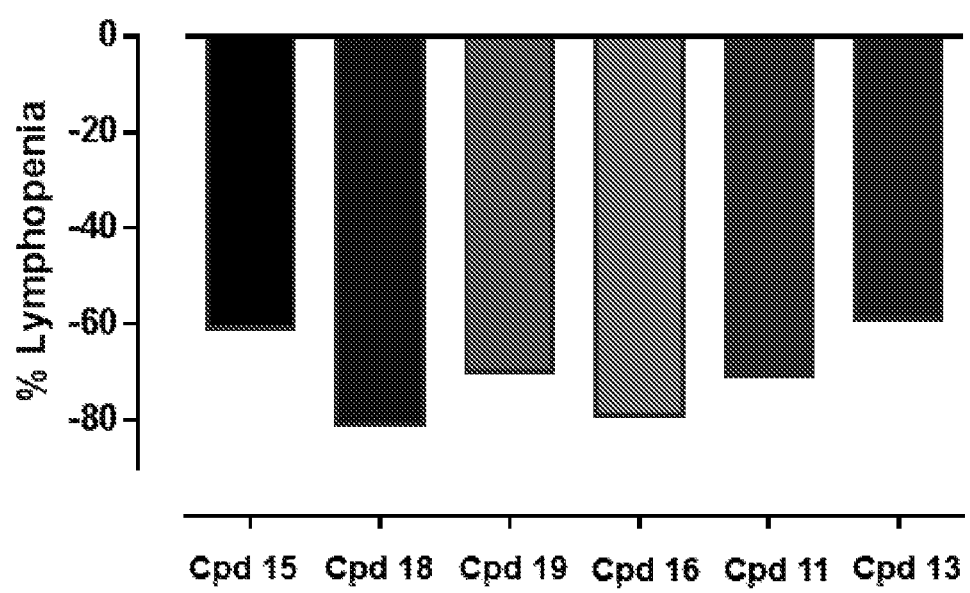
FIG. 2 shows the reduction in lymphocyte count at four hours for compounds of Formula (I) described herein.

A total of 6 mice were used in this study for each compound (Examples 1-6) and divided in two groups as Group 1 (vehicle, Dose: 10 mL/kg) and Group 2 (Compound, Dose: 10 mg/kg, p.o.). Animals in Group 1 were administered with vehicle. Animals in Group 2 were administered with solution formulation of PTC1566-1 at 10 mg/kg dose through oral route. Blood samples from Group 2 were collected under light isoflurane anesthesia from a set of three mice at 1 & 4 hr (p.o.) and from Group 1 blood samples were collected at 4 hr. Plasma was harvested by centrifugation of blood and stored at −70° C. until analysis. Brain was collected at 4 hr from Group 2 animals, weighed and transferred in a poly-propylene tube. Two volumes of PBS buffer (pH 7.4) was added and homogenized to get final volume of 3 times and stored below −70° C. until bioanalysis. Blood sample at 4 hr from both groups were used for lymphocyte count. Analysis Plasma and Brain samples were quantified by fit-for-purpose LCMS/MS method (LLOQ: 4.91 ng/mL for plasma and 14.73 ng/g for brain). For each of the six compounds tested, plasma concentration was greater than 2600 ng/mL at 1 hr and greater than 2100 ng/mL at 4 hr. For each of the six compounds tested, brain concentration was less than 200 ng/g. For each of the six compounds tested (Compound 15, Compound 18, Compound 19, Compound 16, Compound 11, and Compound 13), the lymphocyte count was less than 45% of control (FIG. 2).

Example 20: Phase 3 Study to Evaluate Safety and Efficacy of a Compound of Formula (I), (Ia), (Ib), (Ic), (Id), (Ie), (II), (IIa), (IIb), (IIc), (IId), or (IIe) in Patients with Relapsing Multiple Sclerosis (MS)

The primary objective of this study is to assess tolerability and safety and health outcomes in relapsing MS patients taking a compound of Formula (I), (Ia), (Ib), (Ic), (Id), (Ie), (II), (IIa), (IIb), (IIc), (IId), or (IIe).

Patients:

Eligible patients will be men and women 18 years to 65 years of age.

Criteria:

Inclusion Criteria:

Patients is 18-65 years of age, must have relapsing MS

Exclusion Criteria:

Patients with a type of MS that is not relapsing

Patients with history of chronic immune disease

Patients with a history of certain cancers

Diabetic patients with certain eye disorders

Patients who are on certain immunosuppressive medications or heart medications

Patients with certain heart conditions

Patients with certain lung conditions

Study Type:

Interventional

Study Design:

Intervention Model: Single Group Assignment

Masking: Open Label

Primary Purpose: Treatment

Primary Outcome Measures:

The primary objective of this study is to evaluate the safety and tolerability profile of a compound of Formula (I), (Ia), (Ib), (Ic), (Id), (Ie), (II), (IIa), (IIb), (IIc), (IId), or (IIe) in patients with relapsing forms of MS.

Secondary Outcome Measures:

Incidence of macular edema.

Incidence of bradyarrhythmic electrocardiograms.

Patient reported outcomes indices in multiple sclerosis (PRIMUS), short form health survey-12, and treatment satisfaction questionnaire for medication.

| Condition | Intervention |
|---|---|
| Relapsing Multiple Sclerosis | Compound of Formula (I), (Ia), (Ib), (Ic), (Id), (Ie), (II), (IIa), (IIb), (IIc), (IId), or (IIe) |

What is claimed is:

1. A compound of Formula (I), or a pharmaceutically acceptable salt or solvate thereof:

Formula (I)

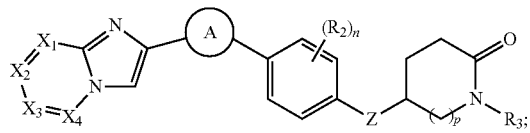

wherein:

$X_1$, $X_2$, $X_3$, and $X_4$ are each $CR_1$;

is selected from

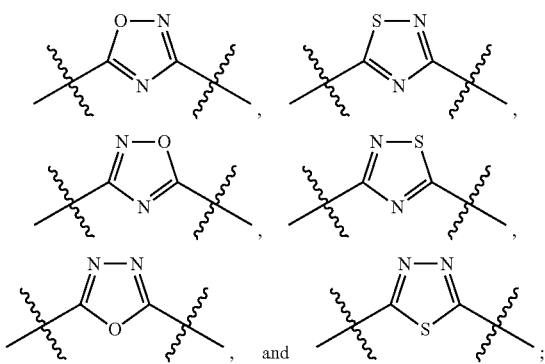

$Z$ is —O—, —S—, —N($R_4$)—, —CH$_2$—, —OCH$_2$—, or —CH$_2$O—;

each $R_1$ is independently selected from the group consisting of hydrogen, halogen, and $CF_3$;

each $R_2$ is independently selected from the group consisting of halogen and optionally substituted $C_1$-$C_6$alkyl;

$R_3$ is selected from the group consisting of hydrogen and optionally substituted $C_1$-$C_6$alkyl;

$R_4$ is hydrogen or optionally substituted $C_1$-$C_6$alkyl;

n is 0-4; and p is 1.

2. The compound of claim 1, or a pharmaceutically acceptable salt or solvate thereof, wherein

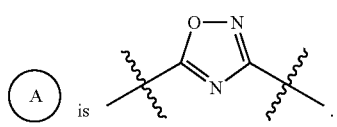

3. The compound of claim 1, or a pharmaceutically acceptable salt or solvate thereof, wherein

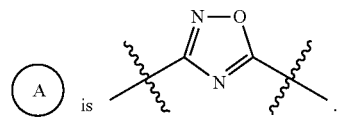

4. The compound of claim 1, or a pharmaceutically acceptable salt or solvate thereof, wherein Z is —O—, —OCH$_2$—, or —CH$_2$O—.

5. The compound of claim 1, or a pharmaceutically acceptable salt or solvate thereof, wherein Z is —O—.

6. The compound of claim 1, or a pharmaceutically acceptable salt or solvate thereof, wherein Z is —OCH$_2$—.

7. The compound of claim 1, or a pharmaceutically acceptable salt or solvate thereof, wherein n is 1 or 2.

8. A pharmaceutical composition comprising a pharmaceutically acceptable diluent, excipient or binder, and a compound of claim 1; or a pharmaceutically acceptable salt or solvate thereof.

9. A method of agonizing sphingosine-1-phosphate (S1P) receptor activity comprising contacting the S1P receptor, or portion thereof, with a compound, or a pharmaceutically acceptable salt or solvate thereof, according to claim 1.

10. A method of treating ulcerative colitis or Crohn's disease in a mammal that would benefit from sphingosine-1-phosphate (S1P) receptor agonism comprising administering to the mammal a therapeutically effective amount of a compound, or a pharmaceutically acceptable salt or solvate thereof, according to claim 1.

11. The compound of claim 1 that is:

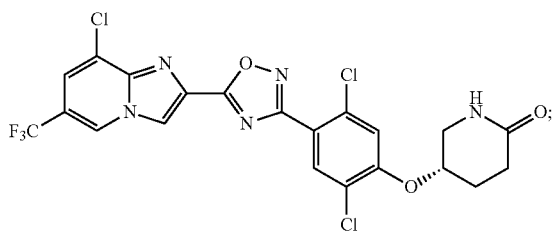 [SMILES: O=C1CC[C@H](Oc2cc(Cl)c(-c3noc(-c4cn5cc(C(F)(F)F)cc(Cl)c5n4)n3)cc2Cl)CN1]

or a pharmaceutically acceptable salt or solvate thereof.

12. The compound of claim 1 that is:

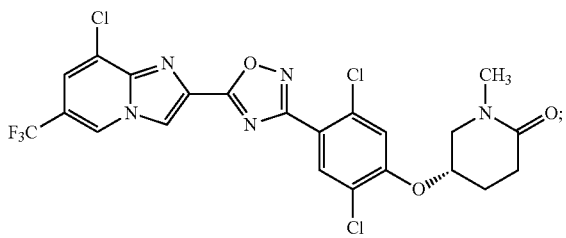 [SMILES: CN1C[C@@H](Oc2cc(Cl)c(-c3noc(-c4cn5cc(C(F)(F)F)cc(Cl)c5n4)n3)cc2Cl)CCC1=O]

or a pharmaceutically acceptable salt or solvate thereof.

13. The compound of claim 1 that is:
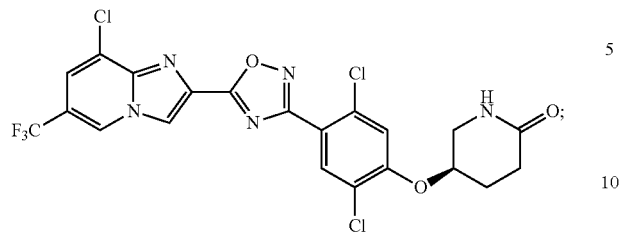
or a pharmaceutically acceptable salt or solvate thereof.
14. The compound of claim 1 that is:
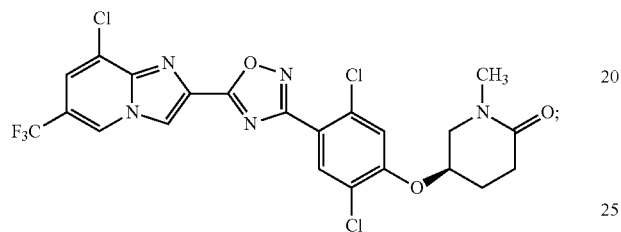
or a pharmaceutically acceptable salt or solvate thereof.
* * * * *